US009066847B2

(12) United States Patent
Poutiatine et al.

(10) Patent No.: US 9,066,847 B2
(45) Date of Patent: Jun. 30, 2015

(54) STORAGE AND DISPENSING DEVICES FOR ADMINISTRATION OF ORAL TRANSMUCOSAL DOSAGE FORMS

(75) Inventors: Andrew I. Poutiatine, San Anselmo, CA (US); Charles Rampersaud, San Francisco, CA (US); Bruce Edwards, Menlo Park, CA (US); Edmond Chiu, San Francisco, CA (US); Stelios Tzannis, Newark, CA (US); Pamela Palmer, San Francisco, CA (US); William Kolosi, San Francisco, CA (US); Sascha Retailleau, San Francisco, CA (US)

(73) Assignee: AceIRx Pharmaceuticals, Inc., Redwood City, CA (US)

( * ) Notice: Subject to any disclaimer, the term of this patent is extended or adjusted under 35 U.S.C. 154(b) by 1670 days.

(21) Appl. No.: 11/825,212

(22) Filed: Jul. 3, 2007

(65) Prior Publication Data

US 2008/0164275 A1    Jul. 10, 2008

Related U.S. Application Data

(63) Continuation-in-part of application No. 11/650,230, filed on Jan. 5, 2007, now Pat. No. 8,357,114.

(51) Int. Cl.
*A61M 31/00* (2006.01)
*A61J 7/00* (2006.01)
(Continued)

(52) U.S. Cl.
CPC .......... *A61J 7/0053* (2013.01); *A61M 37/0069* (2013.01); *A61M 31/007* (2013.01); *A61J 7/0023* (2013.01); *A61J 7/0046* (2013.01); *A61J 7/0076* (2013.01); *A61J 2007/0418* (2013.01); *A61J 2007/0445* (2013.01); *A61M 11/00* (2013.01);
(Continued)

(58) Field of Classification Search
CPC . A61J 7/0053; A61J 7/0076; A61M 37/0069; A61M 31/007
USPC ............... 604/57, 59–64, 73, 77, 275, 514
See application file for complete search history.

(56) References Cited

U.S. PATENT DOCUMENTS 2,621,655 A    12/1952  Olson
3,162,322 A    12/1964  Gilbertson
(Continued)

FOREIGN PATENT DOCUMENTS

EP    1174363         1/2002
EP    1648327 A2      4/2006
(Continued)

OTHER PUBLICATIONS

Bethune-Volters, A Randomlized, Double-Blind Trial Assesssing the Efficacy and Safety of Sublingual Metopimazine and Ondansetron in the Prophyaxis of chemotherapy-Induced Delayed Emesis.
(Continued)

*Primary Examiner* — Theodore Stigell
*Assistant Examiner* — Benjamin Koo

(57) ABSTRACT

Drug storage and dispensing devices for dispensing dosage forms to the oral mucosa of a patient are disclosed. The drug storage and dispensing device is a single dose applicator or a device which includes a means to retard or prevent saliva and/or moisture ingress such that the drug dosage forms in the device remain dry prior to administration.

20 Claims, 18 Drawing Sheets

(51) Int. Cl.
*A61M 37/00* (2006.01)
*G06F 19/00* (2011.01)
*G07F 17/00* (2006.01)
*A61J 7/04* (2006.01)
*A61M 11/00* (2006.01)

(52) U.S. Cl.
CPC ........ *G06F 19/3462* (2013.01); *G07F 17/0092* (2013.01); *A61J 2205/10* (2013.01); *A61J 2205/60* (2013.01)

(56) References Cited

U.S. PATENT DOCUMENTS

| | | | |
|---|---|---|---|
| 3,238,941 A * | 3/1966 | Klein et al. | 604/59 |
| 3,444,858 A | 5/1969 | Russell | |
| 3,757,781 A | 9/1973 | Smart | |
| 3,780,735 A | 12/1973 | Crouter et al. | |
| 3,789,845 A | 2/1974 | Long | |
| 4,020,558 A | 5/1977 | Cournut et al. | |
| 4,060,083 A | 11/1977 | Hanson | |
| 4,229,447 A | 10/1980 | Porter | |
| 4,237,884 A * | 12/1980 | Erickson et al. | 604/57 |
| 4,474,308 A * | 10/1984 | Bergeron | 221/24 |
| 4,489,853 A | 12/1984 | Korte et al. | |
| 4,582,835 A | 4/1986 | Lewis et al. | |
| 4,671,953 A | 6/1987 | Stanley | |
| 4,764,378 A | 8/1988 | Keith et al. | |
| 4,785,969 A | 11/1988 | McLaughlin | |
| 4,863,737 A | 9/1989 | Stanley | |
| 4,873,076 A | 10/1989 | Fishman | |
| 4,880,634 A | 11/1989 | Speiser | |
| 4,950,234 A | 8/1990 | Fujioka et al. | |
| 5,080,903 A | 1/1992 | Ayache | |
| 5,112,616 A | 5/1992 | McCarty | |
| 5,122,127 A | 6/1992 | Stanley | |
| 5,132,114 A | 7/1992 | Stanley | |
| 5,178,878 A | 1/1993 | Wehling | |
| 5,190,185 A | 3/1993 | Blechl | |
| 5,223,264 A | 6/1993 | Wehling et al. | |
| 5,236,714 A | 8/1993 | Lee | |
| 5,263,596 A | 11/1993 | Williams | |
| 5,288,497 A | 2/1994 | Stanley | |
| 5,288,498 A | 2/1994 | Stanley | |
| 5,292,307 A * | 3/1994 | Dolzine et al. | 604/514 |
| 5,296,234 A | 3/1994 | Hadaway | |
| 5,348,158 A | 9/1994 | Honan et al. | |
| 5,366,112 A | 11/1994 | Hinterreiter | |
| 5,366,113 A | 11/1994 | Kim et al. | |
| 5,489,025 A | 2/1996 | Romick | |
| 5,489,689 A | 2/1996 | Mathew | |
| 5,507,277 A | 4/1996 | Rubsamen | |
| 5,507,807 A * | 4/1996 | Shippert | 623/8 |
| 5,549,560 A | 8/1996 | Van de Wijdeven | |
| 5,584,805 A | 12/1996 | Sutton | |
| 5,657,748 A * | 8/1997 | Braithwaite | 128/203.15 |
| 5,660,273 A | 8/1997 | Discko, Jr. | |
| 5,694,919 A | 12/1997 | Rubsamen | |
| 5,710,551 A | 1/1998 | Ridgeway | |
| 5,724,957 A | 3/1998 | Rubsamen | |
| 5,735,263 A | 4/1998 | Rubsamen | |
| 5,752,620 A | 5/1998 | Pearson | |
| 5,785,989 A | 7/1998 | Stanley | |
| 5,800,832 A | 9/1998 | Tapolsky et al. | |
| 5,827,525 A | 10/1998 | Liao | |
| 5,850,937 A | 12/1998 | Rauche | |
| 5,860,946 A | 1/1999 | Hofstatter | |
| 5,945,651 A | 8/1999 | Chorosinski | |
| 5,950,632 A | 9/1999 | Reber et al. | |
| 5,954,641 A | 9/1999 | Kehr et al. | |
| 5,968,547 A | 10/1999 | Reder | |
| 5,981,552 A | 11/1999 | Alam | |
| 5,984,888 A | 11/1999 | Nielsen et al. | |
| 5,992,742 A | 11/1999 | Sullivan et al. | |
| 5,995,938 A | 11/1999 | Whaley | |
| 5,997,518 A | 12/1999 | Laibovitz | |
| 6,024,981 A | 2/2000 | Khankari | |
| 6,039,251 A | 3/2000 | Holowko | |
| 6,116,414 A | 9/2000 | Discko, Jr. | |
| 6,131,765 A | 10/2000 | Barry et al. | |
| 6,171,294 B1 | 1/2001 | Southam et al. | |
| 6,190,326 B1 | 2/2001 | McKinnon | |
| 6,200,604 B1 | 3/2001 | Pather | |
| 6,210,699 B1 | 4/2001 | Acharya | |
| 6,216,033 B1 | 4/2001 | Southam et al. | |
| 6,230,927 B1 | 5/2001 | Schoonen et al. | |
| 6,234,343 B1 | 5/2001 | Papp | |
| 6,248,789 B1 | 6/2001 | Weg | |
| 6,258,056 B1 | 7/2001 | Turley et al. | |
| 6,264,981 B1 | 7/2001 | Zhang et al. | |
| 6,284,512 B1 | 9/2001 | Jones et al. | |
| 6,294,999 B1 | 9/2001 | Yarin et al. | |
| 6,310,072 B1 | 10/2001 | Smith | |
| 6,319,510 B1 | 11/2001 | Yates | |
| 6,328,159 B1 | 12/2001 | Discko, Jr. | |
| 6,350,470 B1 | 2/2002 | Pather | |
| 6,358,944 B1 | 3/2002 | Lederman | |
| 6,364,158 B1 | 4/2002 | Dimoulis | |
| 6,391,335 B1 | 5/2002 | Pather | |
| 6,417,184 B1 | 7/2002 | Ockert | |
| 6,425,495 B1 | 7/2002 | Senda et al. | |
| 6,484,718 B1 | 11/2002 | Schaeffer et al. | |
| 6,488,953 B2 | 12/2002 | Halliday et al. | |
| 6,495,120 B2 | 12/2002 | McCoy | |
| 6,500,456 B1 | 12/2002 | Capella | |
| 6,509,036 B2 | 1/2003 | Pather | |
| 6,541,021 B1 | 4/2003 | Johnson et al. | |
| 6,564,967 B1 | 5/2003 | Stringfield et al. | |
| 6,576,250 B1 | 6/2003 | Pather et al. | |
| 6,605,060 B1 | 8/2003 | O'Neil | |
| 6,641,838 B2 | 11/2003 | Pather | |
| 6,642,258 B1 | 11/2003 | Bourrie | |
| 6,645,528 B1 | 11/2003 | Straub | |
| 6,651,651 B1 | 11/2003 | Bonney et al. | |
| 6,660,295 B2 | 12/2003 | Watanabe et al. | |
| 6,680,071 B1 | 1/2004 | Johnson et al. | |
| 6,682,716 B2 | 1/2004 | Hodges et al. | |
| 6,685,951 B2 | 2/2004 | Cutler | |
| 6,689,373 B2 | 2/2004 | Johnson et al. | |
| 6,726,053 B1 | 4/2004 | Harrold | |
| 6,752,145 B1 | 6/2004 | Bonney et al. | |
| 6,759,059 B1 | 7/2004 | Pettersson | |
| 6,761,910 B1 | 7/2004 | Pettersson | |
| 6,762,684 B1 | 7/2004 | Camhi | |
| 6,764,696 B2 | 7/2004 | Pather | |
| 6,776,978 B2 | 8/2004 | Rabinowitz et al. | |
| 6,793,075 B1 | 9/2004 | Jeter | |
| 6,796,429 B2 | 9/2004 | Cameron | |
| 6,824,512 B2 | 11/2004 | Warkentin | |
| 6,835,194 B2 | 12/2004 | Johnson et al. | |
| 6,855,310 B2 | 2/2005 | Rabinowitz et al. | |
| 6,881,208 B1 | 4/2005 | Phipps et al. | |
| 6,914,668 B2 | 7/2005 | Brestel | |
| 6,932,983 B1 | 8/2005 | Straub | |
| 6,959,808 B2 | 11/2005 | Discko | |
| 6,961,541 B2 | 11/2005 | Overy et al. | |
| 6,963,289 B2 | 11/2005 | Aljadeff et al. | |
| 6,969,508 B2 | 11/2005 | Dugger, III et al. | |
| 6,974,590 B2 | 12/2005 | Pather | |
| 6,999,028 B2 | 2/2006 | Egbert et al. | |
| 7,004,111 B2 | 2/2006 | Olson | |
| 7,018,619 B2 | 3/2006 | Rabinowitz et al. | |
| 7,044,125 B2 | 5/2006 | Vedrine | |
| 7,044,302 B2 | 5/2006 | Conley | |
| 7,070,762 B2 | 7/2006 | Rabinowitz et al. | |
| 7,070,764 B2 | 7/2006 | Rabinowitz et al. | |
| 7,070,765 B2 | 7/2006 | Rabinowitz et al. | |
| 7,072,738 B2 | 7/2006 | Bonney et al. | |
| 7,073,685 B1 | 7/2006 | Giraud et al. | |
| 7,074,935 B2 | 7/2006 | Mathew | |
| 7,078,019 B2 | 7/2006 | Rabinowitz et al. | |
| 7,078,218 B2 | 7/2006 | Smith et al. | |
| 7,090,830 B2 | 8/2006 | Hale et al. | |
| 7,090,866 B2 | 8/2006 | Johnson | |
| 7,118,550 B2 | 10/2006 | Loomis | |

(56) References Cited

U.S. PATENT DOCUMENTS

| | | |
|---|---|---|
| 7,119,690 B2 | 10/2006 | Lerch et al. |
| 7,168,626 B2 | 1/2007 | Lerch et al. |
| 7,172,573 B1 | 2/2007 | Lamb |
| 7,198,172 B2 | 4/2007 | Harvey et al. |
| 7,208,604 B2 | 4/2007 | Mathew |
| 7,215,295 B2 | 5/2007 | Egbert et al. |
| 7,248,165 B2 | 7/2007 | Collins et al. |
| 7,264,139 B2 | 9/2007 | Brickwood et al. |
| 7,276,246 B2 | 10/2007 | Zhang et al. |
| 7,295,890 B2 | 11/2007 | Jean-Pierre |
| 7,306,812 B2 | 12/2007 | Zhang et al. |
| 7,458,374 B2 | 12/2008 | Hale et al. |
| 7,468,179 B2 | 12/2008 | Rabinowitz et al. |
| 7,484,642 B2 | 2/2009 | Bonney et al. |
| 7,500,444 B2 | 3/2009 | Bonney et al. |
| 7,537,005 B2 | 5/2009 | Dave |
| 7,540,998 B2 | 6/2009 | Terwilliger et al. |
| 7,552,728 B2 | 6/2009 | Bonney et al. |
| 7,581,657 B2 | 9/2009 | Dickmann |
| 7,744,558 B2 | 6/2010 | Maag |
| 8,062,248 B2 | 11/2011 | Kindel |
| 8,142,733 B2 | 3/2012 | Creaven |
| 8,753,308 B2 | 6/2014 | Palmer et al. |
| 8,778,393 B2 | 7/2014 | Palmer et al. |
| 8,778,394 B2 | 7/2014 | Palmer et al. |
| 8,905,964 B2 | 12/2014 | Poutiatine et al. |
| 2001/0020147 A1 | 9/2001 | Staniforth et al. |
| 2002/0026330 A1 | 2/2002 | Klein |
| 2002/0037491 A1 | 3/2002 | Halliday |
| 2002/0071857 A1 | 6/2002 | Kararli et al. |
| 2002/0110578 A1 | 8/2002 | Pather et al. |
| 2002/0142050 A1 | 10/2002 | Straub |
| 2002/0160043 A1 | 10/2002 | Coleman |
| 2003/0008005 A1 | 1/2003 | Cutler |
| 2003/0015196 A1 | 1/2003 | Hodges et al. |
| 2003/0015197 A1 | 1/2003 | Hale |
| 2003/0017175 A1 | 1/2003 | Cutler |
| 2003/0017994 A1 | 1/2003 | Cutler |
| 2003/0022910 A1 | 1/2003 | Cutler |
| 2003/0035776 A1 | 2/2003 | Hodges |
| 2003/0052135 A1 | 3/2003 | Conley |
| 2003/0052787 A1 | 3/2003 | Zerhusen et al. |
| 2003/0077300 A1 | 4/2003 | Wermeling et al. |
| 2003/0091629 A1 | 5/2003 | Pather et al. |
| 2003/0099158 A1 | 5/2003 | De La Huerga |
| 2003/0130314 A1 | 7/2003 | Druzgala |
| 2003/0132239 A1 | 7/2003 | Konig |
| 2003/0173408 A1 | 9/2003 | Mosher et al. |
| 2003/0185872 A1 | 10/2003 | Kochinke |
| 2003/0190290 A1 | 10/2003 | Ross |
| 2003/0232080 A1 | 12/2003 | Pather et al. |
| 2004/0017567 A1 | 1/2004 | Loicht et al. |
| 2004/0025871 A1 | 2/2004 | Davies |
| 2004/0034059 A1 | 2/2004 | Grarup et al. |
| 2004/0037882 A1 | 2/2004 | Johnson |
| 2004/0080515 A1 | 4/2004 | Hagiwara |
| 2004/0092531 A1 | 5/2004 | Chizh |
| 2004/0094564 A1 | 5/2004 | Papp |
| 2004/0111053 A1* | 6/2004 | Nicolette ............ 604/59 |
| 2004/0120896 A1 | 6/2004 | Dugger |
| 2004/0133305 A1* | 7/2004 | Jean-Pierre ............ 700/231 |
| 2004/0158349 A1 | 8/2004 | Bonney et al. |
| 2004/0170567 A1 | 9/2004 | Sackler |
| 2004/0180080 A1 | 9/2004 | Furusawa |
| 2004/0191178 A1 | 9/2004 | Cutler |
| 2004/0213855 A1 | 10/2004 | Pettersson |
| 2004/0248964 A1 | 12/2004 | Crooks |
| 2004/0253307 A1 | 12/2004 | Hague et al. |
| 2005/0038062 A1 | 2/2005 | Burns |
| 2005/0049464 A1 | 3/2005 | Lassers |
| 2005/0054942 A1 | 3/2005 | Melker et al. |
| 2005/0064030 A1 | 3/2005 | Pather et al. |
| 2005/0065175 A1 | 3/2005 | Gonzales et al. |
| 2005/0089479 A1 | 4/2005 | Rabinowitz et al. |
| 2005/0101936 A1 | 5/2005 | Gonzales et al. |
| 2005/0122219 A1 | 6/2005 | Petersen et al. |
| 2005/0131386 A1 | 6/2005 | Freeman et al. |
| 2005/0142197 A1 | 6/2005 | Moe |
| 2005/0142198 A1 | 6/2005 | Moe |
| 2005/0150488 A1 | 7/2005 | Dave |
| 2005/0150489 A1 | 7/2005 | Dunfield et al. |
| 2005/0163838 A1 | 7/2005 | Moe |
| 2005/0169989 A1 | 8/2005 | Moe et al. |
| 2005/0176790 A1 | 8/2005 | Bartholomaus |
| 2005/0258066 A1 | 11/2005 | Conley |
| 2006/0026035 A1 | 2/2006 | Younkes |
| 2006/0031099 A1 | 2/2006 | Vitello et al. |
| 2006/0039959 A1 | 2/2006 | Wessling |
| 2006/0045865 A1 | 3/2006 | Jacob |
| 2006/0062812 A1 | 3/2006 | Ross |
| 2006/0067978 A1 | 3/2006 | Heiler |
| 2006/0089858 A1 | 4/2006 | Ling |
| 2006/0134200 A1 | 6/2006 | Vandoni et al. |
| 2006/0216352 A1 | 9/2006 | Nystrom |
| 2006/0229570 A1 | 10/2006 | Lovell |
| 2006/0247578 A1 | 11/2006 | Arguedas et al. |
| 2006/0292219 A1 | 12/2006 | Pather |
| 2007/0020186 A1 | 1/2007 | Stroppolo |
| 2007/0031502 A1 | 2/2007 | Pettersson |
| 2007/0036853 A1 | 2/2007 | Agarwal |
| 2007/0071806 A1 | 3/2007 | McCarty |
| 2007/0074722 A1 | 4/2007 | Giroux |
| 2007/0104763 A1 | 5/2007 | Jobdevairakkam et al. |
| 2007/0185084 A1 | 8/2007 | McKinney |
| 2007/0186923 A1 | 8/2007 | Poutiatine et al. |
| 2007/0190130 A1 | 8/2007 | Mark |
| 2007/0207207 A1 | 9/2007 | Tzannis et al. |
| 2007/0260491 A1 | 11/2007 | Palmer et al. |
| 2007/0286900 A1 | 12/2007 | Herry et al. |
| 2007/0299687 A1 | 12/2007 | Palmer et al. |
| 2008/0147044 A1 | 6/2008 | Palmer et al. |
| 2008/0166404 A1 | 7/2008 | Tzannis et al. |
| 2008/0203107 A1 | 8/2008 | Conley et al. |
| 2008/0268023 A1 | 10/2008 | Palmer et al. |
| 2009/0010992 A1 | 1/2009 | Palmer et al. |
| 2009/0048237 A1 | 2/2009 | Palmer et al. |
| 2009/0131479 A1 | 5/2009 | Palmer et al. |
| 2010/0105735 A1 | 4/2010 | Palmer et al. |
| 2010/0130551 A1 | 5/2010 | Pushpala et al. |
| 2010/0137836 A1 | 6/2010 | Palmer et al. |
| 2010/0253476 A1 | 10/2010 | Poutiatine et al. |
| 2010/0256190 A1 | 10/2010 | Palmer et al. |
| 2011/0091544 A1 | 4/2011 | Palmer |
| 2011/0288128 A1 | 11/2011 | Palmer et al. |
| 2012/0035216 A1 | 2/2012 | Palmer et al. |
| 2012/0232473 A1 | 9/2012 | Poutiatine et al. |
| 2013/0158074 A1 | 6/2013 | Palmer et al. |
| 2013/0165481 A1 | 6/2013 | Palmer et al. |

FOREIGN PATENT DOCUMENTS

| | | |
|---|---|---|
| EP | 1261316 B1 | 4/2008 |
| EP | 1257311 B1 | 12/2008 |
| EP | 2114383 B1 | 7/2010 |
| GB | 2309966 | 8/1997 |
| JP | 2000-142841 | 5/2000 |
| JP | 2003-525081 | 8/2003 |
| JP | 2007-517636 | 7/2007 |
| WO | WO 00/16750 | 3/2000 |
| WO | WO 00/57858 | 10/2000 |
| WO | WO 00/66458 | 11/2000 |
| WO | WO 01/30288 | 5/2001 |
| WO | WO 01/64182 | 7/2001 |
| WO | WO 01/97780 | 12/2001 |
| WO | WO 02/32487 | 4/2002 |
| WO | WO 02/074372 | 9/2002 |
| WO | WO 02/078594 | 10/2002 |
| WO | WO 03/092575 | 11/2003 |
| WO | WO 2004/069198 | 8/2004 |

(56) References Cited

FOREIGN PATENT DOCUMENTS

| WO | WO2004080515 | 9/2004 |
|---|---|---|
| WO | WO 2006/097361 | 9/2006 |

OTHER PUBLICATIONS

Brendenberg, "New Concepts in Administration of Drugs in Tablet Form—Formulations and Evaluation of a Sublingual Tablet for Rapid Absorption, and Presentation of an Individualised Dose Administration System", Comprehensive Summaries of Uppsala Dissertations from the Faculty of Pharmacy 287, ACTA Universitatis Upsaliensis Uppsala.

Chauvin, M., "Sufentanil Pharmacokinetics in Patients With Cirrhosis", Anesthes Analg, 1989, 68(1):1-4.

Coluzzi P.H., et al., Breakthrough Cancer Pain: A Randomized Trial Comparing Oral Transmucosal Fentanyl Citrate (OTFC) and Morphine Sulfate Immediate Release (MSIR), Pain, 2001, 91(1-2):123-130.

Farnsworth, S.T., et al., "Ocular Transmucosal Absorption and Toxicity of Sufentanil in Dogs", Anesth Analg, 1998, 86:138-140.

Gardner-Nix J., "Oral Transmucosal Fentanyl and Sufentanil for Incident Pain", J Pain Symptom Management, Aug. 2001, 22(2):627-630.

Geldner, G., et al., "Comparison Between Three Transmucosal Routes of Administration of Midazolam in Children", Paediatr Anaesth, 1997, 7(2):103-109.

Gerak, L.R., "Studies on Benzodiazepines and Opioids Administered Alone and in Combination in Rhesus Monkeys: Ventilation and Drug Discrimination", Psychopharmacology, 1998, 137:164-174.

Gordon, D.B., Oral Transmucosal Fentanyl Citrate for Cancer Breakthrough Pain: A Review, Oncol Nurs Forum, Nov. 3, 2006, 33(2)257-264.

Gram-Hansen P., "Plasma Concentrations Following Oral and Sublingual Administration of Lorazepam", Int J. Clin Pharmacol Ther Toxical, 1988, 26(6):323-324.

Haynes, G., "Plasma Sufentantil Concentration After Intranasal Administration to Paediatric Outpatients", Can J. Anaesth, 1993, 40(3):286.

Helmers, et al., 1989, Can J. Anaesth, 1989, 6:494-497.

Jackson K., et al., "Pilot Dose Finding Study of Intranasal Sufentanil for Breakthrough and Incident Cancer-Associated Pain", J Pain Symptom Manage, 2002, 23(6):450-452.

Restriction Requirement for U.S. Appl. No. 11/825,212, mailed Dec. 9, 2009.

Office Action for U.S. Appl. No. 11/825,251, mailed Dec. 15, 2009.
Office Action for U.S. Appl. No. 11/650,227, mailed Dec. 15, 2009.
Office Action for U.S. Appl. No. 11/429,904, mailed Aug. 20, 2009.
Office Action for U.S. Appl. No. 11/473,551, mailed Sep. 11, 2009.
Office Action for U.S. Appl. No. 11/650,227, mailed Sep. 21, 2009.
Office Action for U.S. Appl. No. 11/650,230, mailed Aug. 4, 2009.
Office Action for U.S. Appl. No. 11/974,092, mailed Sep. 30, 2009.

International Search Report and Written Opinion dated Dec. 17, 2007 issued in PCT/2007/00527 (WO/2007/081947).

International Search Report and Written Opinion dated Feb. 4, 2008 issued in PCT/2007/00528 (WO/2007/081948).

Berthold et.al.; "Comparison of sublingually and orally administered triazolam for premedication before oral surgery";*Oral Surg Oral Med Oral Pathol Oral Radiol Endod*; 1997; 84(2):119-24.

Bredenberg et al; "In vitro and in vivo evaluation of a new sublingual tablet system for rapid or mucosal absorption using fentanyl citrate as the active substance"; *European Journal of Pharmaceutical Sciences*; 2003; 327-334.

KGH Drug Information Service; "Sublingual Sufentanil for Incident Pain"; *KGH Drug Information Bulletin*, vol. 37(4) 2, 2004.

Odou et al.; "Pharmacokinetics of midazolam: comparison of sublingual and intravenous routes in rabbit"; *Eur J Drug Metab Pharmacokinet*; 1999; 24(1):1-7.

Stopperich et al.; "Oral triazolam pretreatment for intravenous sedation"; *Anesth Prog.* 1993;40(4):117-21.

Yeomans et al.; "Sublingual Sufentanil"; *Vancouver Hospital and Health Science Center Drug and Therapeutics Newsletter*, vol. 8(1) 2, 2001.

Abrams, R. et al., "Safety and effectiveness of intranasal administration of sedative medications (ketamine, midazolam, or sufentanil) for urgent brief pediatric dental procedures," Anesth. Prog., 40:63-66 (1993).

AcelRx Pharmaceuticals, Inc., "AcelRx Pharmaceuticals Reports Positive Results from a Clinical Trial of Sublingual Sufentanil/Triazolam NanoTabTM Combination (ARX-03) in Treating Procedural Pain and Anxiety," Jan. 12, 2009, pp. 1-2.

ACTIQ® Fact Sheet (Mar. 2004).

AHFS Drug Information, Sufentanil Citrate, 28:08.08, 2157-2160 (2007).

Ahmad, S. et al., "Fentanyl HCl iontophoretic transdermal system versus intravenous morphine pump after gynecologic surgery," Arch Gynecol Obstet 276:251-258 (2007).

Albert, J. M. et al., "Patient-controlled analgesia vs. conventional intramuscular analgesia following colon surgery," Diseases of the Colon & Rectum, 31(2):83-86 (1988).

Anlar, S. et al., "Formulation and in vitro-in vivo evaluation of buccoadhesive morphine sulfate tablets," Pharmaceutical Research, 11(2):231-236 (1994).

Bayrak, F. et al., "A comparison of oral midazolam, oral tramadol, and intranasal sufentanil premedication in pediatric patients," Journal of Opioid Management, 3(2):74-78 (2007).

Bovill, J. G. et al., "The pharmacokinetics of sufentanil in surgical patients," Anesthesiology, 61:502-506 (1984).

Brusset, A. et al., "Comparative pharmacokinetic study of fentanyl and sufentanil after single high-bolus doses," Clin Drug Invest, 18(5):377-389 (1999).

Chelly, J. E. et al., "The safety and efficacy of a fentanyl patient-controlled transdermal system for acute postoperative analgesia: a multicenter, placebo-controlled trial," Anesth. Analg., 98:427-433 (2004).

Christie, J. M. et al., "Dose-titration, multi-center study of oral transmucosal fentanyl citrate for the treatment of breakthrough pain in cancer patients using transdermal fentanyl for persistent pain," J Clin Oncol., 16(10):3238-45 (1998).

Coda, B. A. et al., "Comparative efficacy of patient-controlled administration of morphine, hydromorphone, or sufentanil for the treatment of oral mucositis pain following bone marrow transplantation," Pain, 72:333-346 (1997).

Collins, L. M. C. et al., "The surface area of the adult human mouth and thickness of the salivary film covering the teeth and oral mucosa," J. Dent. Res., 66(8):1300-1302 (1987).

Culling et al., "Haemodynamics and plasma concentrations following sublingual GTN and intravenous, or inhaled isosorbide dinitrate," Br. J. Clin. Pharm., 17:125-131 (1984).

Dale, O. et al., "Nasal Administration of Opioids for Pain Management in Adults," Acta Anaesthesiol. Scand., 46:759-770 (2002).

Darwish, M. et al., "Single-Dose and Steady-State Pharmacokinetics of Fentanyl Buccal Tablet in Healthy Volunteers," Journal of Clinical Pharmacology, 47(1):56-63 (2007).

Darwish, M. et al., "Pharmacokinetics and dose proportionality of fentanyl effervescent buccal tablets in healthy volunteers," Clinical Pharmacokinetics, 44(12):1279-1286 (2005).

Darwish, M. et al., "Comparison of equivalent doses of fentanyl buccal tablets and arteriovenous differences in fentanyl pharmacokinetics," Clinical Pharmacokinetics, 45(8):843-350 (2006).

Darwish, M. et al., "Pharmacokinetic properties of fentanyl effervescent buccal tablets: a phase I, open-label, crossover study of single-dose 100, 200, 400, and 800 μg in healthy adult volunteers," Clinical Therapeutics, 28(5):707-714 (2006).

Darwish, M. et al., "Relative bioavailability of the fentanyl effervescent buccal tablet (FEBT) 1080 μg versus oral transmucosal fentanyl citrate 1600 μg and dose proportionality of FEBT 270 to 1300 μg: a single-dose, randomized, open-label, three-period study in healthy adult volunteers," Clinical Therapeutics, 28(5):715-724 (2006).

Darwish, M. et al., "Effect of buccal dwell time on the pharmacokinetic profile of fentanyl buccal tablet," Expert Opin. Pharmacother., 8(13):2011-2016 (2007).

(56) References Cited

OTHER PUBLICATIONS

Darwish, M. et al., "Bioequivalence following buccal and sublingual placement of fentanyl buccal tablet 400 µg in healthy subjects," Clin. Drug Invest., 28(1):1-7 (2008).
Darwish, M. et al., "Absolute and Relative Bioavailability of Fentanyl Buccal Tablet and Oral Transmucosal Fentanyl Citrate," Journal of Clinical Pharmacology, 47:343-350 (2007).
De Castro, J. et al., "Practical applications and limitations of analgesic anesthesia," Acta Anesthesiologica Belgica, 3:107-128 (1976).
De Vries, M. E. et al., "Developments in buccal drug delivery," Critical Reviews in Therapeutic Drug Carrier Systems, 8(3):271-303 (1991).
Demeules, J. et al., "Clinical pharmacology and rationale of analgesic combinations," European Journal of Anaesthesiology, 20(28):7-12 (2003).
Drug Information Bulletin [online], 37(4) (Sep./Oct. 2004), [Retrieved on Jun. 5, 2008.] Retrieved from the Internet: <URL: http://www.kgh.on.ca/pharmacy/diBulletinSeptOct2004.pdf>, 4 pages.
Durfee, S. et al., "Fentanyl effervescent buccal tablets. Enhanced buccal absorption," American Journal of Drug Delivery, 4(1):1-5 (2006).
Egan, T. D. et al., "Multiple dose pharmacokinetics of oral transmucosal fentanyl citrate in healthy volunteers," Anesthesiology, 92:665-673 (2000).
Ellmauer, S., "Sufentanil: An alternative to fentanyl/alfentanil?" Anaesthesist, 43(3):143-158 (1994).
Enting, R. H. et al., "The 'pain pen' for breakthrough cancer pain: a promising treatment," Journal of Pain and Symptom Management, 29(2):213-217 (2005).
FDA Guidance for Industry: Container Closure Systems for Packaging Human Drugs and Biologics, pp. 1-E2 (1999).
Fentora™ Package Insert (2006).
Fentora®, 2008 Red Book, p. 174.
Fisher, D. M. et al., "Pharmacokinetics of an implanted osmotic pump delivering sufentanil for the treatment of chronic pain," Anesthesiology, 99(4):929-937 (2003).
Grass, J., "Patient-controlled analgesia," Anesth. Analg., 101:S44-S61 (2005).
Griffin, D. et al., Reg. Anesth. Pain Med., vol. 10, American Society of Regional Anesthesia Spring Meeting (2010).
Guay, J. et al., "Pharmacokinetics of sufentanil in normal children," Canadian Journal of Anaesthesia, 39(1):14-20 (1992).
Halliburton, J. R., "The pharmacokinetics of fentanyl, sufentanil and alfentanil: a comparative review," Journal of the American Association of Nurse Anesthetists, 56(3):229-233 (1988).
Hazardous Substances Data Bank (HSDB) [online] [Retrieved from the Internet]. URL: http://toxnet.nlm.nih.gov. Apr. 9, 2007, Name: Sufentanil; RN: 56030-54-7, 26 pages.
Helmers, J. H. et al., "Sufentanil pharmacokinetics in young adult and elderly surgical patients," European Journal of Anaesthesiology, 11(3):181-185 (1994).
Henderson, J. M. et al., "Pre-induction of anesthesia in pediatric patients with nasally administered sufentanil," Anesthesiology, 68:671-675 (1988).
Heshmati, F. et al., "Intranasal sufentanil for postoperative pain control in lower abdominal pediatric surgery," Iranian Journal of Pharmacology & Therapeutics, 5:131-133 (2006).
Hicks, R. et al., "USP Medication Safety Forum: Medication Errors Involving Patient-Controlled Analgesia," Joint Commission on Quality and Patient Safety, 34(12):734-742 (2008).
Ikinci, G. et al., "Development of buccal bioadhesive nicotine tablet formulation for smoking cessation," International Journal of Pharmaceutics, 277(1-2):173-178 (2004).
Infusion Pump Improvement Initiative, Center for Devices and Radiological Health, U.S. Food and Drug Administration, Apr. 2010, 7 pages.
Karl, H. W. et al., "Pharmacokinetics of oral triazolam in children," Journal Clinical Psychopharmacology, 17(3):169-172 (1997).
Keohane, C. A. et al., "Intravenous medication safety and smart infusion systems," Journal of Infusion Nursing, 28(5):321-328 (Sep./Oct. 2005).
Kotey, G. A. et al., "Iontophoretic delivery of fentanyl for acute post-operative pain management," The European Journal of Hospital Pharmacy Science, 13(1):3-9 (2007).
Kress, H. G. et al., "Efficacy and tolerability of intranasal fentanyl spray 50 to 200 µg for breakthrough pain in patients with cancer: a phase III, multinantional, randomized, double-blind, placebo-controlled, crossover trial with a 10-month, open-label extension treatment period," Clinical Therapeutics, 31(6): 1171-1191 (2009).
Lehmann, K. A. et al., "Postoperative patient-controlled analgesia with sufentanil: analgesic efficacy and minimum effective concentrations," Acta Anaesthesiol Scand., 35:221-226 (1991).
Lehmann, K. A. et al., "Pharmacokinetics of sufentanil in general surgical patients under different conditions of anesthesia," Acta Anaesthesiol Scand., 37:176-180 (1993).
Lim, T. W. et al., "Premedication with midazolam is more effective by the sublingual than oral route," Canadian Journal of Anaesthesia, 44(7):723-726 (1997).
Lin, L. et al., "Applying human factors to the design of medical equipment: patient-controlled analgesia," J. Clin. Monitoring and Computing, 14:253-263 (1998).
Mather, L. E., "Clinical pharmacokinetics of fentanyl and its newer derivatives," Clinical Pharmacokinetics, 8:422-446 (1983).
McInnes, F. et al., "Evaluation of the clearance of a sublingual buprenorphine spray in the beagle dog using gamma scintigraphy," Pharmaceutical Research, (2007), 6 pages.
Mendelson, J. et al., "Bioavailability of Sublingual Buprenorphine," The Journal of Clinical Pharmacology, 37:31-37 (1997).
Miaskowski, C., "Patient-controlled modalities for acute postoperative pain management," Journal of PeriAnesthesia Nursing, 20(4):255-267 (Aug. 2005).
Miller, R. D., "The pursuit of excellence. The 47th Annual Rovenstine Lecture," Anesthesiology, 110(4):714-720 (Apr. 2009).
Minkowitz et al., Reg. Anesth. Pain Med., vol. 8, American Society of Regional Anesthesia Spring Meeting (2010).
Molander, L. et al., "Pharmacokinetic investigation of a nicotine sublilngual tablet," Eur. J. Clin. Pharmacol., 56(11):813-819 (2001).
Moment, M. et al., "Patient-controlled analgesia in the management of postoperative pain," Drugs, 66(18):2321-2337 (2006).
Motwani, J. G. et al., "Clinical pharmacokinetics of drugs administered buccally and sublingually," Clin. Pharmacokinet., 21(2):83-94 (1991).
Mystakidou, K. et al., "Oral transmucosal fentanyl citrate: overview of pharmacological and clinical characteristics," Drug Delivery, 13(4):269-276 (2006).
Nath, R. P. et al., "Buprenorphine pharmacokinetics: relative bioavailability of sublingual tablet and liquid formulations," The Journal of Clinical Pharmacology, 39:619-623 (1999).
Onsolis Package Insert (Jul. 2009), 11 pages.
Paix, A. et al., "Subcutaneous fentanyl and sufentanil infusion substitution for morphine intolerance in cancer pain management," Pain, 63:263-269 (1995).
Paradis et al., "Solid-phase microextraction of human plasma samples for determination of sufentanil by gas chromatography-mass spectrometry," Therapeutic Drug Monitoring, 24:768-774 (2002).
Pavlin, D. J. et al., "Effects of combining propofol and alfentanil on ventilation, analgesia, sedation, and emesis in human volunteers," Anesthesiology, 84(1):23-37 (1996)—Abstract.
Portenoy, R. K. et al., "A randomized, placebo-controlled study of fentanyl buccal tablet for breakthrough pain in opioid-treated patients with cancer," The Clinical Journal of Pain, 22(9):805-811 (2006).
Portenoy, R. K. et al., "Oral transmucosal fentanyl citrate (OTFC) for the treatment of breakthrough pain in cancer patients: a controlled dose titration study," Pain, 79:303-312 (1999).
Puig, M. M. et al., "Sufentanil pharmacokinetics in neurosurgical patients," International Journal of Clinical Pharmacology, Therapy and Toxicology, 27(5):229-234 (1989).
Rawal, N. et al., "Current practices for postoperative pain management in Europe and the potential role of the fentanyl HCl iontophoretic transdermal system," European Journal of Anaesthesiology, 24:299-308 (2007).

(56) References Cited

OTHER PUBLICATIONS

Raza, S. M. A. et al., "Haemodynamic stability with midazolam-ketamine-sufentanil analgesia in cardiac patients," Can. J. Anaesth., 36(6):617-623 (1989).
Reisfield, G. M. et al., "Rational use of sublingual opioids in palliative medicine," Journal of Palliative Medicine, 10(2):465-475 (2007).
Reynolds, L. et al., "Relative analgesic potency of fentanyl and sufentanil during intermediate-term infusions in patients after long-term opiod treatment for chronic pain," Pain, 110:182-188 (2004).
Rosati, J. et al., "Evaluation of an oral patient-controlled analgesia device for pain management in oncology inpatients," J. Support. Oncol., 5(9):443-448 (2007).
Rosow, C. E., "Sufentanil Citrate: A New Opioid Analgesic for Use in Anesthesia," Pharmacotherapy, 4:11-19 (1984).
Rothschild, J. M. et al., "A controlled trial of smart infusion pumps to improve medication safety in critically ill patients," Crit. Care Med., 33(3):533-540 (2005).
Roy, S. D. et al., "Solubility behavior of narcotic analgesics in aqueous media: solubilities and dissociation constants of morphine, fentanyl and sufentanil," Pharmaceutical Research, 6(2):147-151 (1989).
Sanford et al., "A comparison of morphine, fentanyl, and sufentanil anesthesia for cardiac surgery: induction, emergence, and extubation," Anesthesia and Analgesia, 65:259-266 (1986).
Savoia, G. et al., "Sufentanil: an overview of its use for acute pain management," Minerva Anestesiologica, 67(9 Suppl 1):206-216 (2001).
Scavone, J. M. et al., "Alprazolam kinetics following sublingual and oral administration," J. Clin. Psychpharmacol., 7(5):332-334 (1987).
Scholz, J. et al., "Clinical pharmacokinetics of alfentanil, fentanyl and sufentanil," Clin. Pharmacokinet., 31(4):275-292 (1996).
Shojaei, A. H. et al., "Buccal mucosa as a route for systemic drug delivery: a review," Journal of Pharmacy and Pharmaceutical Sciences, 1:15-30 (1998).
Siepmann, J. et al., "Calculation of the required size and shape of hydroxypropyl methylcellulose matrices to achieve desired drug release profiles," International Journal of Pharmaceutics, 201(1):151-164 (2000).
Slatkin et al., "Fentanyl Buccal Tablet for Relief of Breakthrough Pain in Opioid-Tolerant Patients With Cancer-Related Chronic Pain," J. of Supportive Oncol., vol. 5, No. 7, Jul./Aug. 2007, pp. 327-334.
Smith, R. B. et al., "Temporal variation in traizolam pharmacokinetics and pharmacodynamics after oral administration," The Journal of Clinical Pharmacology, 26(2):120-124 (1986).
Streisand, J. B. et al., "Absorption and bioavailability of oral transmucosal fentanyl citrate," Anesthesiology, 75:223-229 (1991).
Streisand, J. B. et al., "Dose proportionality and pharmacokinetics of oral transmucosal fentanyl citrate," Anesthesiology, 88(2):305-309 (1998).
Striebel, H. W. et al., "Patient-controlled intranasal analgesia (PCINA) for the management of postoperative pain: a pilot study," Journal of Clinical Anesthesia, 8:4-8 (1996).
Striebel, H. W. et al., "Patient-controlled intranasal analgesia: a method for noninvasive postoperative pain management," Anesth Analg, 83:548-851 (1996).
SUFENTA® Package Insert (2006), 3 pages.
Vadivelu, N. et al., "Recent advances in postoperative pain management," Yale Journal of Biology and Medicine, 83:11-25 (2010).
Van de Walle, J. et al., "Double blind comparison of fentanyl and sulfentanil in anesthesia," Acta Anaesthesiologica Belgica, 27(3):129-138 (1976).
Van Raders, P. et al., "Nurses' views on ease of patient care in postoperative pain management," British Journal of Nursing, 16(5):312-317 (2007).
Vasight, N. et al., "Formulation selection and pharmacokinetic comparison of fentanyl buccal soluble film with oral transmucosal fentanyl citrate," Clin. Drug Investig., 29(10):647-654 (2009).
Vercauteren, M. P. et al., "Epidural sufentanil for postoperative patient-controlled analgesia (PCA) with or without background infusion: a double-blind comparison," Anesth. Analg., 80:76-80 (1995).
Viscusi, E. R. et al., "An iontophoretic fentanyl patient-activated analgesic delivery system for postoperative pain: a double-blind, placebo-controlled trial," Anesth Analg., 102(1):188-194 (2006).
Viscusi, E. R. et al., "Patient-controlled transdermal fentanyl hydrochloride vs intravenous morphine pump for postoperative pain: a randomized controlled trial," JAMA, 291(11):1333-1341 (2004).
Viscusi, E. R., "Patient-controlled drug delivery for acute postoperative pain management: a review of current and emerging technologies," Regional Anesthesia and Pain Medicine, 33(2):146-158 (2008).
Walder, B. et al., "Analgesia and sedation in critically ill patients," Swiss Med. Wkly., 134(23-24):333-346 (2004).
International Search Report and Written Opinion for International Application No. PCT/US2011/037401, mailed Aug. 19, 2011.
Office Action for U.S. Appl. No. 12/580,930, mailed Oct. 21, 2011.
International Search Report and Written Opinion for International Application No. PCT/US2010/027437, mailed Jun. 21, 2010.
Office Action for U.S. Appl. No. 13/416,236, mailed Feb. 4, 2013.
Office Action for U.S. Appl. No. 12/275,485, mailed Mar. 2, 2011.
Office Action for U.S. Appl. No. 12/275,485, mailed Nov. 23, 2011.
International Search Report and Written Opinion for International Application No. PCT/US2009/064232, mailed Mar. 17, 2010.
Office Action U.S. Appl. No. 11/429,904, mailed Sep. 17, 2008.
Office Action U.S. Appl. No. 11/429,904, mailed Mar. 5, 2009.
International Search Report and Written Opinion for International Application No. PCT/US2007/010822, mailed Aug. 5, 2008.
Office Action U.S. Appl. No. 11/473,551, mailed Sep. 26, 2008.
Office Action U.S. Appl. No. 11/473,551, mailed Mar. 16, 2009.
International Search Report and Written Opinion for International Application No. PCT/US2007/011337, mailed Aug. 21, 2008.
Office Action for U.S. Appl. No. 12/187,937, mailed Sep. 16, 2010.
International Search Report and Written Opinion for International Application No. PCT/US2008/072445, mailed Oct. 20, 2008.
Office Action for U.S. Appl. No. 11/650,227, mailed Dec. 9, 2008.
Office Action for U.S. Appl. No. 11/650,227, mailed Jul. 6, 2009.
Office Action for U.S. Appl. No. 11/650,227, mailed Aug. 5, 2010.
Office Action for U.S. Appl. No. 11/825,251, mailed Sep. 21, 2009.
Office Action for U.S. Appl. No. 11/825,251, mailed Aug. 5, 2010.
Office Action for U.S. Appl. No. 11/650,174, mailed Oct. 13, 2010.
Office Action for U.S. Appl. No. 11/650,174, mailed Jun. 14, 2011.
Written Opinion for International Application No. PCT/US2007/000529, mailed Sep. 11, 2007.
International Preliminary Report on Patentability for International Application No. PCT/US2007/000529, dated Jul. 8, 2008.
Office Action for Canadian Application No. 2,636,115, dated Feb. 12, 2013.
Supplementary European Search Report for European Application No. 07716450, mailed Apr. 6, 2011.
Office Action for Japanese Patent Application No. 2008-549610, mailed Nov. 25, 2011.
Office Action for Japanese Patent Application No. 2008-549610, mailed Nov. 15, 2012.
Office Action for U.S. Appl. No. 11/650,230, mailed Sep. 25, 2008.
Office Action for U.S. Appl. No. 11/650,230, mailed Mar. 10, 2009.
Office Action for U.S. Appl. No. 11/650,230, mailed Feb. 2, 2010.
Office Action for U.S. Appl. No. 11/650,230, mailed Jun. 16, 2010.
Office Action for U.S. Appl. No. 11/650,230, mailed Mar. 1, 2011.
Office Action for U.S. Appl. No. 11/650,230, mailed Mar. 27, 2012.
International Preliminary Report on Patentability for International Application No. PCT/US2007/000527, dated Feb. 24, 2009.
Office Action for Canadian Application No. 2,673,880, mailed May 6, 2014.
Office Action for Chinese Patent Application No. 200780051996.7, mailed Feb. 23, 2012.
Office Action for Japanese Patent Application No. 2009-544898, mailed Jul. 24, 2012.
International Search Report and Written Opinion for International Application No. PCT/US2007/089016, mailed Jun. 17, 2008.
International Preliminary Report on Patentability for International Application No. PCT/US2007/089016, dated Jul. 7, 2009.

(56) References Cited

OTHER PUBLICATIONS

Office Action for U.S. Appl. No. 11/974,092, mailed Mar. 31, 2010.
Office Action for U.S. Appl. No. 11/974,092, mailed Jun. 13, 2011.
Office Action for Canadian Application No. 2,673,837, mailed Apr. 24, 2014.
First Examination Report for Indian Application No. 2436/KOLNP/2009 dated Aug. 5, 2014.
Notice of Reasons for Rejection for Japanese Application No. 2009-544899, mailed Aug. 1, 2012.
Notice of Final Rejection for Japanese Application No. 2009-544899, mailed Jul. 29, 2013.
Office Action for U.S. Appl. No. 11/980,216, mailed Dec. 24, 2008.
Office Action for U.S. Appl. No. 11/980,216, mailed Jul. 20, 2009.
Office Action for U.S. Appl. No. 11/980,216, mailed Jan. 5, 2010.
Office Action for U.S. Appl. No. 11/980,216, mailed Jul. 2, 2010.
Office Action for U.S. Appl. No. 11/980,216, mailed Jun. 19, 2014.
International Search Report and Written Opinion for International Application No. PCT/US2007/089017, mailed Jun. 23, 2008.
International Preliminary Report on Patentability for International Application No. PCT/US2007/089017, dated Jul. 7, 2009.
Office Action for U.S. Appl. No. 11/985,162, mailed Dec. 20, 2010.
International Search Report and Written Opinion for International Application No. PCT/US2007/089018, mailed Oct. 15, 2008.
European Search Report for European Application No. 13161632, mailed Feb. 6, 2014.
Notice of Grounds for Rejection for Korean Patent Application No. 2014-7008364, issued May 28, 2014.
Office Action for U.S. Appl. No. 12/521,983, mailed Feb. 15, 2012.
Office Action for U.S. Appl. No. 13/744,448, mailed Jul. 15, 2013.
Office Action for U.S. Appl. No. 13/744,448, mailed Apr. 9, 2014.
European Search Report for European Application No. 14177156.8, mailed Nov. 5, 2014.
Office Action for Japanese Application No. 2013-246090, mailed Dec. 2, 2014.
Jackson, "Pharmacokinetics and Clinical Effects of Multidose Sublingual Triazolam in Healthy Volunteers" J Clin Psychopharmacol, Feb. 2006, 26(1):4-8.
James, et al., "The Use of a Short-Acting Benzodiazepine to Reduce the Risk of Syncopal Episodes During Upright Sterotactic Breast Biopsy", Clin Radiol, Mar. 2005, 60(3):394-396.
Jeannet, et al., "Home and Hospital Treatment of Acute Seizures in Children with Nasal Midazolam", Eur J. Paediatr Neurol, 1999, 3(2):73-77.
Kaplan, G.B., "Single Dose Pharmacokinetics and Pharmacodynamics of Alprazolam in Elderly and Young Subjects", PubMed, 1998, 38(1):14-21.
Karl, et al., "Comparison of the Safety and Efficacy of Intranasal Midazolam of Sufentanil for Preinduction of Anesthesia in Pediatric Patients", Anesthesiology, 1992, 76:209-215.
Karl, H.W., Transmucosal Administration of Midazolam for Premedication of Pediatric Patients, Anesthesiology, 1993, 78(5):885-891.
Khalil, et al., "Sublingual Midazolam Premedication in Children: A Dose Response Study", Paediatr Anaesth, 1998, 8(6):461-465.
Kogan, et al., "Premedication with Midazolam in Young Children: A Comparison of four Routes of Administration", Paediatr Anaesth Oct. 2002, 12(8):685-689.
Kontinen, et al., "Premedication With Sublingual Triazolam Compared With Oral Diazepam", Canadian Journal of Anesthesia, 1993, 40:829-834.
Kroboth, P.D., "Triazolam Pharmacokinetics After Intravenous, Oral and Sublingual Administration", J Clin Psychophamacol, 1995, 15(4):259-262.
Kunz, K.M., "Severe Episodic Pain: Management With Sublingual Sufentanil", Journal of Pain and Symptom Management, 1993, 8:189-190.
Lennernäs B., "Pharmacokinetics and Tolerability of Different Doses of Fentanyl Following Sublingual Administration of a Rapidly Dissolving Tablet to Cancer Patients: A New Approach to Treatment of Incident Pain", Br J Clin Pharmacol, Feb. 2005, 59(2):249-253.
Lichtor, J.L., "The Relative Potency of Oral Transmucosal Fentanyl Citrate (OTFC) Compared With Intravenous Morphine in the Treatment of Moderate to Severe Postoperative Pain" Anesth Anal, 1999, 89(3):732-738.
Lipworth, et al., Pharmacokinetics, Effacacy and Adverse Efects of Sublingual Salbutamol in Patients with Asthma, European Journal of Clinical Pharmacology, Nov. 1989, 37(6).
Mathieu, N., et al., "Intranasal Sufentanil is Effective for Postoperative analgesia in Adults", Can J Anesth, 2006, 53(1):60-66.
McCann and Kain, "The Management of Preoperative Anxiety in Children: an Update", Anesthesia & Analgesia, 2001, 93:98-105.
Monk, J.P., "Sufentanil: A Review of Its Pharmacological Properties and Therapeutic Use", Drugs, 1988, 36:286-313.
Naguib, et al. "The Comparative Dose-Response Effects fo Melatonin and Midazolam for Premedication of Adult Patients: A Double-Blinded, Placebo-Controlled Study", Anesth Analg, Aug. 2000, 91(2):473-479.
Odou, C., et al., "Development of Midazolam Sublingual Tablets: In Vitro Study", Eur J Drug Metab Pharmacokinet, Apr.-Jun. 1998, 23(2):87-91.
Okayama, et al, "Bronchodilator Effect of Sublingual Isosorbide Dinitrate in Asthma", Eur J Clin Pharmacol, 1984, 26(2):151-155.
Roy, S.D., "Transdermal Delivery of Narcotic Analgesics: pH, Anatomical, and Subject Influences on Cutaneous Permeability of Fentanyl and Sufentanil", Pharm Res, 1990, 7:842-847.
Scavone, J.M., "The Pharmacokinectics and Pharmacodynamics of Sublingual and Oral Alprazolam in the Post-Pradial State", Eur J Clin Pharmacol, 1992, 42(4):439-443.
Scavone, J.M., et al, "Enhanced Bioavailibility of Triazolam Following Sublingual Versus Oral Administration", J Clin Pharmacol, Mar. 1986, 26(3):208-210.
Schreiber, K.M., "The Association of Preprocedural anxiety and the Success of Procedural Sedation inChildren", Am J Emerg Med, Jul. 2006, 24(4):397-401.
Schwagmeier, R., "Midazolam Pharmacokinetics Following Intravenous and Buccal Administration", Br J Clin Pharmacol, 1998, 46:203-206.
Sinatra, R.S., "Patient-Controlled Analgesia with Sufentanil: A Comparison of Two Different Methods of Administration", Journal of Clinical Anesthesia, 1996, 8:123-129.
Tweedy, C.M., "Pharmacokinetics and Clinical Effects of Sublingual Triazolam in Pediatric Dental Patients" J Clin Psychopharmacol, 2001, 21(3):268-272.
Vercauteren M., "Intranasal Sufentanil for Pre-Operative Sedation", Anaesthesia, 1988, 43(4):270-273.
Viitanen, et al, "Medazolam Premedication Delays Recovery from Propofol-Induced Sevoflurane Anesthesia in Children 1-3 yr", Canadian Journal of Anaesthesia, 1999, 46:766-71.
Weniberg, D.S., Sublingual Absorption of Selected Opioid Analgesics, Clin Parmacol Ther, Sep. 1988, 44(3):335-342.
Wheeler, M., "Uptake Pharmacokinetics of the Fentanyl Oralet in Children Scheduled for Central Venous Access Removal: Implications for the timing of Initiating Painful Procedures", Paediatric Anesthesia, 2002, 12:594-599.
Willens, J.S., "Pharmacodynamics, Pharmacokinetics, and Clinical Uses of Fentanyl, Sufentanil, and Alfentanil", Heart and Lung, 1993, 22:239-251.
Yager J.Y., "Sublingual Lorazepam in Childhood Serial Seizures", Am J Dis Child, 1988, 142:931-932.
Zedie, N., "Comparison of Intranasal Midazolam and Sufentanil Premedication in Pediatric Outpatients", Clin Parmacol and Therapeutics, 1996, 59:341-348.
Zhang, H., "Oral Mucosal Drug Delivery: Clinical Pharmacokinetics and Therapeutic Applications", Clinical Pharmacokinetics, 2002, 41(9):661-680(20).

* cited by examiner

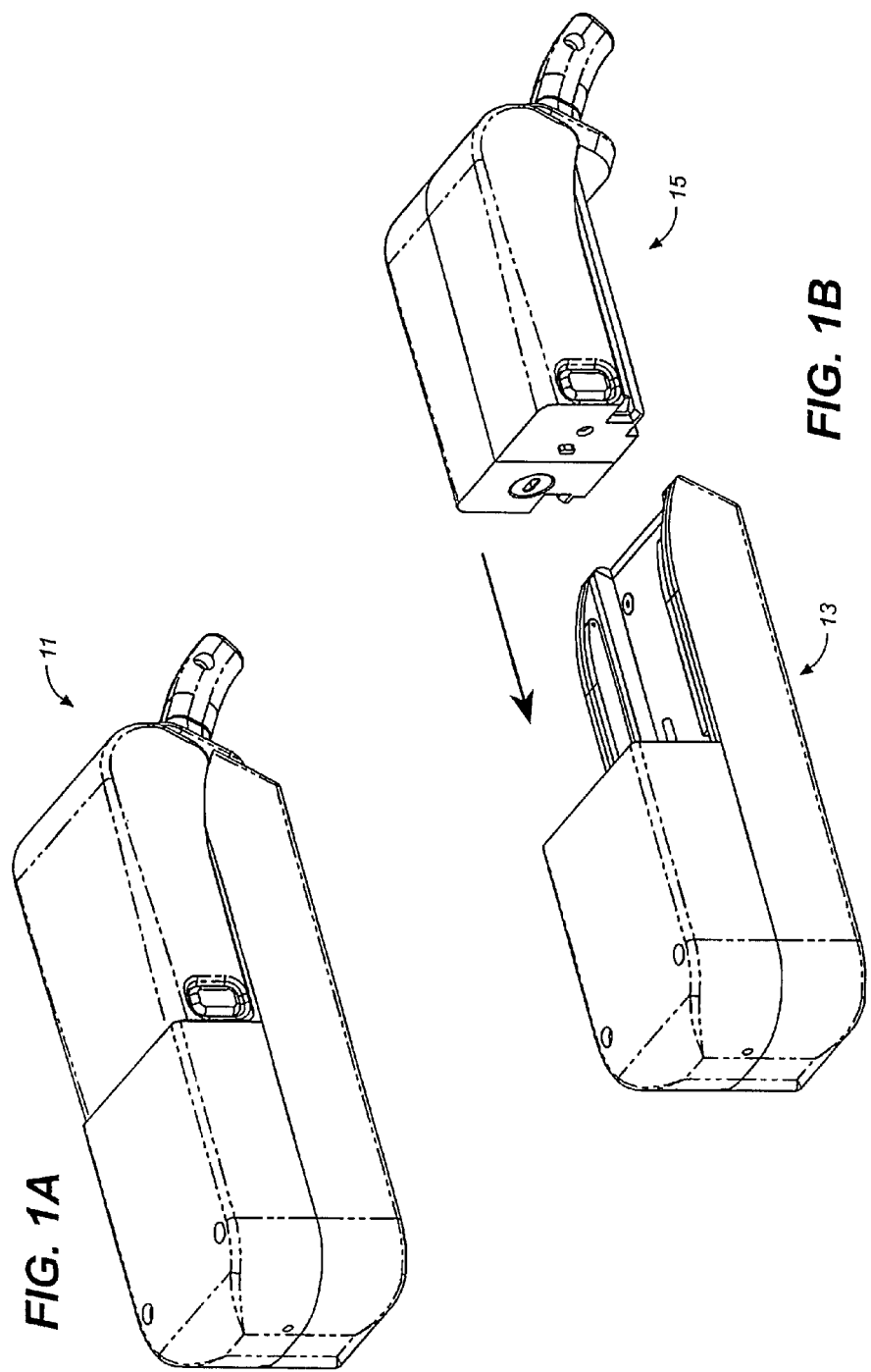

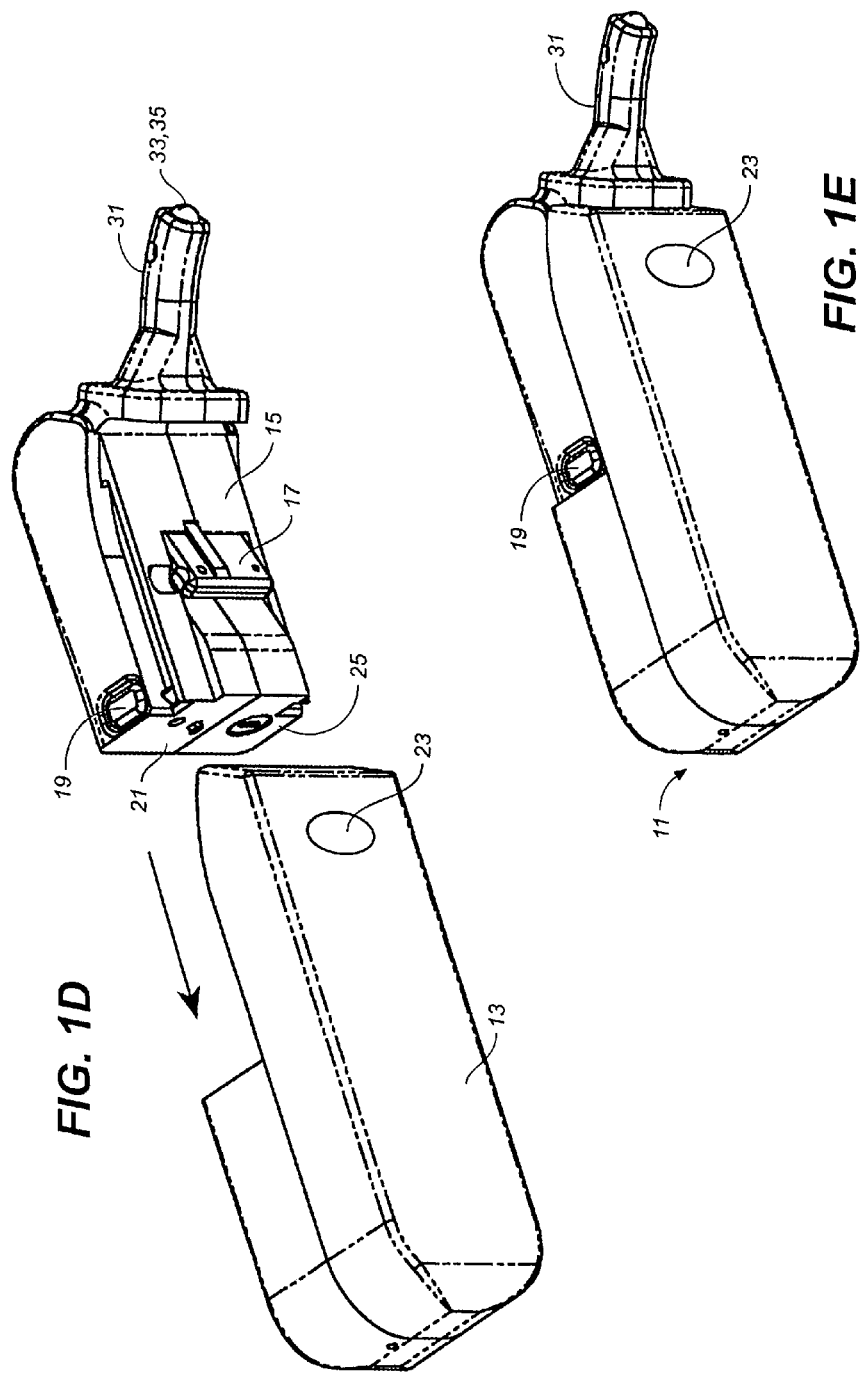

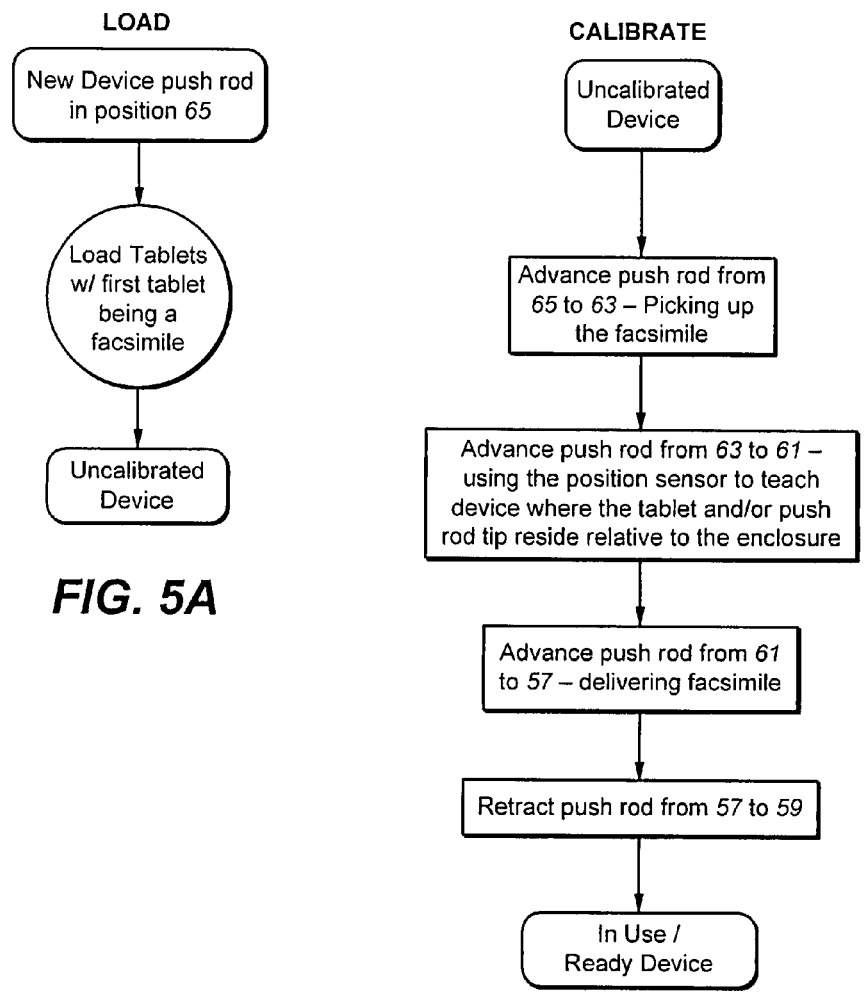

FIG. 15A          FIG. 15B

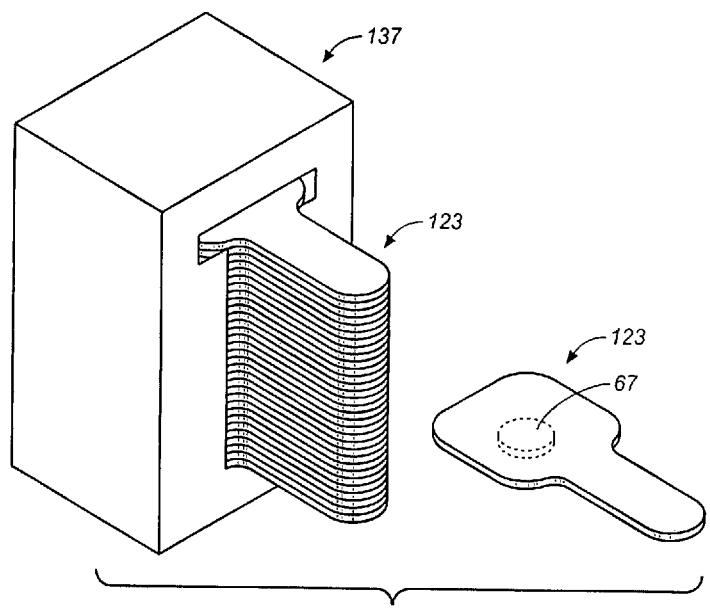
FIG. 17
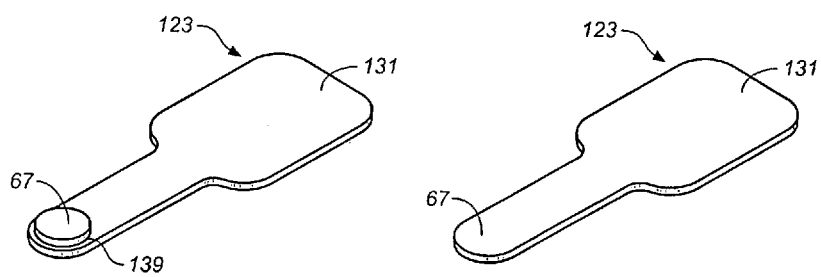
FIG. 18A  FIG. 18B

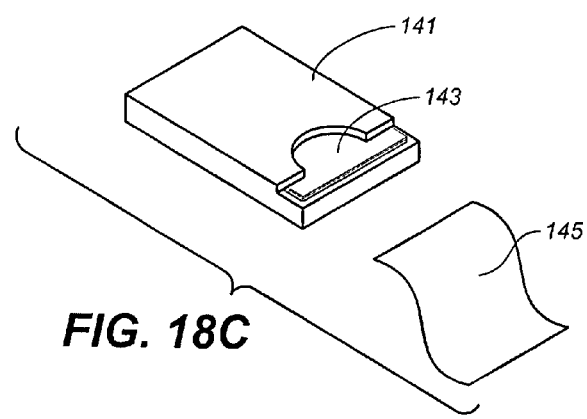
FIG. 18C
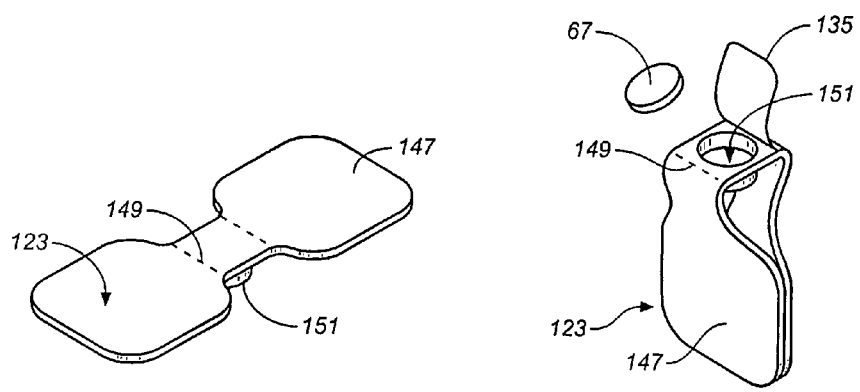
FIG. 19A  FIG. 19B

STORAGE AND DISPENSING DEVICES FOR ADMINISTRATION OF ORAL TRANSMUCOSAL DOSAGE FORMS

CROSS REFERENCE TO OTHER APPLICATIONS

This application claims the priority benefit of U.S. patent application Ser. No. 11/650,230, filed Jan. 5, 2007, which is incorporated herein by reference in its entirety.

FIELD OF THE INVENTION

The present invention relates to dispensing devices and systems for oral transmucosal administrations of small volume drug dosage forms. The dispensing devices are handheld and portable and are either single dose applicators or comprise a means for blocking or retarding saliva ingress and/or moisture control. The dispensing devices further provide for appropriate placement of small volume oral transmucosal dosage forms to maximize drug delivery via the oral mucosa.

BACKGROUND OF THE INVENTION

There are advantages to delivering medications via the oral mucosa and drug formulation, delivery and dispensing technology for such medications represents an area of active research. Controlled drug delivery systems offer numerous advantages as compared to current drug delivery systems, which include controlled delivery, improved safety, improved patient compliance and convenience.

U.S. Pat. No. 7,044,302, issued May 16, 2006 and US Patent Publication No. 20030052135 (Conley; Avancen), entitled "Patient controlled timed oral medication drug dispensing device", describe an oral medication delivery device for administration of an as-needed medication, where the device has programmed drug accessibility with lock-out.

U.S. Pat. No. 6,234,343, issued May 22, 2001 (Papp; Papp Enterprises, LLC), entitled "Automated portable medication radial dispensing apparatus and method", describes a portable medication cartridge that allows for both manual and automated (microprocessor controlled) dispensing of tablets or capsules of virtually all sizes through a radial dispensing apparatus, where the medication is sequentially advanced and allowed to radically dispense through an open side of the tablet tray from the medication cartridge.

U.S. Pat. No. 5,945,651 discloses a medication dispensing system including a relatively small, microprocessor-controlled machine that assists in the accurate execution of a physician-prescribed medication regimen. The machine can be used as a stand-alone unit, or can be integrated into a centrally-controlled pharmaceutical network.

The relevant art does not describe a dispensing device that provides a means for delivery of a dosage form to the oral mucosa where the device facilitates proper placement of the medication and the dosage form is protected from saliva.

Although currently available drug dispensing devices have been effective in the administration of a variety of types of drugs, there remains a need for improved devices for administration of drugs to the oral mucosa wherein the device can be used multiple times while preserving the integrity of the drug stored within. There is also a need for a device that can be use to self administer such dosage forms wherein the device provides for safe and controlled delivery.

There is, therefore, substantial interest in the development of improved devices and systems for drug delivery to the oral mucosa in both the hospital and out-patient settings.

SUMMARY OF THE INVENTION

A handheld portable dispensing device for administration of a drug dosage form to the oral mucosa of a subject, wherein the device has a housing having a dispensing end and a means to prevent or retard saliva or moisture ingress is provided.

The drug dosage form typically has bioadhesive characteristics and the dispensing device is effective to place a dosage form on the oral mucosa, e.g., in the sublingual space.

The device can dispense multiple doses, a single dose at a time and is partially or fully disposable. The device may have a reusable head and a disposable body.

The dispensing device has a number of component parts, including: a proboscis comprising a shroud, a replaceable cartridge (which houses drug dosage forms and may be disposable), and a pushrod, e.g., a flexible pushrod.

The cartridge may comprise one or more shipping tablets and sufficient drug dosage forms for 1 to 5 days of treatment, e.g., sufficient drug dosage forms for 2 to 3 days of treatment.

Operation of the dispensing device may be manual or electromechanical.

The dispensing device may further comprise one or more of: a lock-out feature, may be child resistant, may comprise a means for recording dosing history and a means to view or download the dosing history wherein the dosing history is resettable, may comprise a means for dosage form detection wherein the device is capable of detecting when one or more shipping tablets or dosage forms has been dispensed, is capable of distinguishing between a shipping tablet and a dosage form, and may comprise a means for self-calibration of the dispense mechanism and a means of connectivity for data transfer. Furthermore, the dispensing device may comprise one or more means of uni-directionally or bi-directionally communicating with a drug dosage form cartridge (e.g. the cartridge uploads drug and dosing information to the dispensing device upon loading the cartridge into the device.)

The invention further provides methods of using a dispensing device of the invention and systems comprising the same.

The invention further provides disposable single dose applicators (SDAs) for dispensing a drug dosage form to the oral mucosa of a subject.

A typical SDA of the invention is an applicator having an applicating end portion and a handle (or other means for holding the device), wherein the applicating end portion comprises a covered blister or holder for the dosage form.

The cover may be foil, plastic or paper and may cover the applicating end portion alone or both the applicating end portion and the handle or other means of holding the device.

The invention further provides methods of using an SDA and systems comprising the same.

Application of a dispensing device or SDA of the invention is not limited to any particular type of drug or patient population. As such, the dispensing devices and SDAs of the present invention find utility in drug delivery to pediatric, adult and non-human mammalian subjects.

BRIEF DESCRIPTION OF THE DRAWINGS

FIGS. 1A-E provide a schematic depiction of an exemplary dispensing device of the invention wherein the device is designed to deliver drug dosage forms to oral mucosa of a patient under treatment. FIGS. 1A-E illustrate the progression of intact drug dispensing device 11 (FIG. 1A); the reusable head 13 and disposable body 15 of a drug dispensing device (FIG. 1B); a reusable head 13, disposable body 15 and cartridge 17, a dispense button 23, and a proboscis 31 of a drug dispensing device (FIG. 1C); various aspects of a drug dispensing device 11 including a reusable head 13, disposable body 15 and cartridge 17, a proboscis 31, and a latch 19 to unlock the device, a hub lock 21, a distal seal 33, 35, and a power train coupling 25 (FIG. 1D); and a reassembled intact drug dispensing device 11 (FIG. 1E).

FIGS. 5A-D provide a series of flow diagrams for use of an exemplary device of the invention showing the stages of push rod/tablet interaction during device use, wherein FIG. 5A shows the LOAD feature; FIG. 5B shows the CALIBRATE feature; FIG. 5C shows the DISPENSE feature; and FIG. 5D shows the DISASSEMBLE feature.

In FIG. 6, the push rod 51, dosage forms 67, shipping tablet 69, spring 73 and position sensor 71 are shown. During use, the push rod 51 moves between positions 57, 59, 61, 63, 65 and 67, also shown in FIG. 6.

FIGS. 15A-C provide an illustration of one type of single dose applicator and use thereof in delivering a dosage form to a subject.

FIG. 17 provides an illustration of a multiple dose applicator where a plurality of single dose applicators are stored prior to use.

FIGS. 18A-C provide an illustration of additional single dose applicator and multiple dose applicator embodiments.

FIGS. 19A-B provide an illustration of two stages of use of one embodiment of a single dose applicator.

DETAILED DESCRIPTION OF THE INVENTION

Figure 1C:
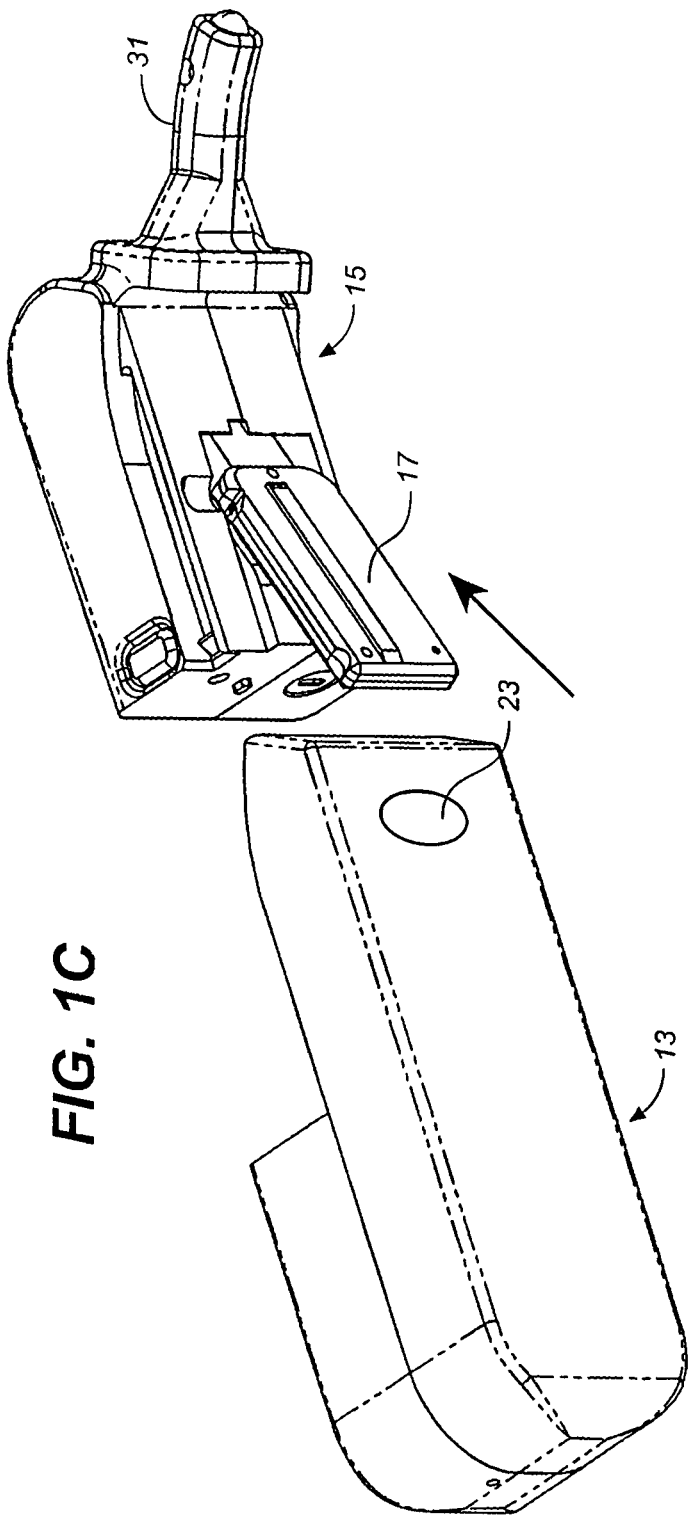

The following disclosure describes the dispensing devices, systems and methods which constitute the present invention. A detailed disclosure of the devices, systems and methods of the present invention for administration of a drug dosage are provided herein below. The present invention generally encompasses: (1) drug dispensing devices; (2) a system that includes a dispensing device and drug dosage forms; and (3) methods for using such dispensing devices and systems.

The present invention is generally directed to dispensing devices for dispensing any of a number of types of dosage forms to the oral mucosa, methods of using such dispensing devices and systems comprising the same. The invention is not limited to the specific devices, systems and methodology or syndromes described herein, as these may, of course, vary. It is also to be understood that the terminology used herein is for the purpose of describing particular embodiments only, and is not intended to limit the scope of the present invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

It must be noted that as used herein and in the appended claims, the singular forms "a", "and", and "the" include plural references unless the context clearly dictates otherwise. Thus, for example, reference to "a drug formulation" includes a plurality of such formulations and reference to "a drug delivery device" includes systems comprising drug formulations and devices for containment, storage and delivery of such formulations.

All publications referred to herein are incorporated herein by reference in their entirety for the purpose of describing and disclosing the compositions and methodologies which are described in the publications which might be used in connection with the presently described invention. The publications discussed herein are provided solely for their disclosure prior to the filing date of the present application. Nothing herein is to be construed as an admission that the invention is not entitled to antedate such a disclosure by virtue of prior invention.

Definitions

The terms "formulation" and "drug formulation" or "drug dosage form" as used herein refer to a physical composition containing at least one therapeutic agent, which may be provided in any of a number of dosage forms for delivery to a subject. The dosage form may be provided to the patient as a lozenge, pill, capsule, membrane, strip, liquid, patch, film, gum, gel, spray or other form.

The term "drug" as used herein is generally meant to refer to any substance that alters the physiology of an animal. The term "drug" may be used interchangeably herein with the terms "therapeutic agent", "medication", "pharmacologically active agent" and the like. It will be understood that a "drug" formulation of the invention may include more than one therapeutic agent, wherein exemplary combinations of therapeutic agents include a combination of two or more drugs.

The term "subject" includes any subject, generally a mammal (e.g., human, canine, feline, equine, bovine, ungulate etc.), adult or child, in which treatment for a disorder is desired. The terms "subject" and "patient" may be used interchangeably herein.

The term "transmucosal" delivery of a drug and the like is meant to encompass all forms of delivery across or through a mucous membrane. In particular, "oral transmucosal" delivery of a drug includes delivery across any tissue of the mouth, pharynx, larynx, trachea, upper respiratory tract or upper gastrointestinal tract, particularly including the sublingual, gingival and palatal mucosal tissues.

The term "oral transmucosal drug delivery" as used herein refers to a dosage form wherein drug delivery occurs substantially via the transmucosal route and not via swallowing followed by GI absorption. Such dosage forms are designed to provide for a dissolution rate that allows for maximal delivery via the oral mucosa, typically via placement of the dosage form in the sublingual location.

As used herein, "sublingual", means literally "under the tongue" and refers to a method of administering substances via the mouth in such a way that the substances are rapidly absorbed via the blood vessels under the tongue rather than via the digestive tract. Absorption occurs via highly vascularized buccal mucosa and allows a substance more direct access to the blood circulation, providing for direct systemic administration independent of gastrointestinal influences The term "treatment" or "management" of a medical disorder or condition is used herein to generally describe regression, suppression, or mitigation of symptoms of the medical disorder or condition so as to make the subject more comfortable as determined by subjective criteria, objective criteria, or both.

The term "diversion" is used here to generally describe the act or an instance of diverting the use of a dispensing device and/or drug dosage forms therein from the intended patient to any other unauthorized or unintended individual, whether it is accidental or intentional diversion.

"Operatively connected" as used herein means the components are provided in a device so as to function as intended to achieve an aim. For example, a memory device operatively connected to a CPU which is further operatively connected to a release mechanism may be meant to indicate that, upon actuation, the CPU communicates with the memory device to check the status or history of drug delivery, and then further communicates with the release mechanism (e.g., via a solenoid and a switch) to release and dispense a drug.

The term "fob" refers to a small, portable handheld, powered electronic docking device that can be used in conjunction with the drug dispensing device to upload data, download data, control access to the drug dispensing device, control access to the drug dosage forms, or enhance or otherwise alter the user interface of the drug dispensing device. A fob may communicate and dock with a drug dispensing device either in a wired or wireless fashion. A fob may be adapted to attach to a cord so as to allow the fob to hang from the neck of a healthcare professional such as a physician or caregiver, particularly in the hospital setting. A drug dispensing device may communicate with the physician or care giver via the fob.

The terms "dispensing device", "drug dispensing device", "dispenser", "drug dispenser", "drug dosage dispenser" and "drug delivery device" are used interchangeably herein with the term "dispensing device" and refer to a device that dispenses a drug dosage. A single dose applicator is considered a "drug dispensing device". The dispensing device provides a mechanism for controlled and safe delivery of the medication formulated in the dosage forms of the invention to the oral mucosa of a patient and is adapted for storage and/or delivery of a dosage form such as a lozenge, pill, tablet, capsule, membrane, strip, liquid, patch, film, gel, spray or other form.

The term "systems that include a drug dosage form and a dispensing device" as used herein refers to a drug dispensing system for delivery and/or monitoring of drug administration. A system of the invention may be used to monitor and deliver both efficacious and maximum dosages such that the amount of drug delivered, corresponding efficacy and safety are enhanced over currently available systems. The system may have one or more features that provide for improved safety and ease of use over currently available systems including a security feature that prevents unauthorized access to the stored drugs, a theft deterrent feature that helps prevent theft, a dosing lock-out feature, a dose counting feature, a memory means for retaining information about dose delivery, and an interface for bidirectional exchange of information with a user, a drug cartridge, or another device such as a computer, and a means for identifying an individual patient for controlled drug access.

The term "proboscis" is used interchangeably with the terms "dispensing tip" a "delivery tip", and refers to a dispensing and/or positioning tip of a drug dosage form dispenser that delivers a dosage form to a desired location (e.g. the oral mucosa).

The term "shroud" is used to describe a partial or complete covering of the delivery port of the proboscis to protect the delivery port from contact with saliva or other moisture in the oral cavity.

Features of Dispensing Devices of the Invention

In one embodiment, a drug dispensing device of the invention is handheld and portable.

In another embodiment, the device is capable of dispensing multiple drug dosage forms a single dose at a time for delivery via the oral mucosa, e.g., into the sublingual space.

The drug dispensing device has a housing having a dispensing end which typically has a proboscis with a shroud or other means to means to block or retard saliva ingress, as further described herein below.

In some embodiments of the invention, the drug dispensing device is actuated manually and fully disposable.

In other embodiments of the invention, the drug dispensing device is actuated by an electromechanical means.

Drug dispensing devices of the invention have a number of additional features, further described below.

Blocking/Retarding Saliva and Moisture Ingress

A device of the invention comprises a means for minimizing or eliminating saliva ingress and moisture ingress into the dispensing device: (1) to avoid wetting the dosage forms therein; (2) to isolate any saliva that enters the dispensing device in such a manner that the dosage forms therein remain dry; (3) to absorb or adsorb any saliva that enters the dispensing device in such a manner that the dosage forms remain dry; (4) to block saliva and moisture from entering the device, to protect the dosage forms from vapor and liquid phase moisture, or (5) any combination thereof.

A device of the invention comprises a means for preventing and/or controlling humidity ingress due to ambient conditions outside of the device.

The means for minimizing or eliminating saliva ingress or preventing other moisture from entering the dispensing device includes, but is not limited to, one or more flexible or rigid seals, one or more flexible or rigid wipers, use of one or more absorbent material components such as a desiccant or pad, a door or latch that is manually or automatically opened and closed, multiple stage delivery systems, a positive air pressure and airflow, or an air gap or prescribed distance or barrier/shroud maintained between the tablet delivery orifice and the mucus membrane tissues within the mouth that may transport the saliva. The shroud limits the ability of the tongue or sublingual mucosa to contact the dosage form dispensing area, thereby controlling saliva contact and ingress. By inhibiting or eliminating the "wetness" inside the shroud and on the surface of the valve/seal, the dosage form is dispensed without adhesion occurring between the dosage form and the shroud or valve/seal. The drug dispensing devices of the invention provide a means for minimizing or eliminating saliva ingress into the dispensing device during administration of the drug to the oral mucosa of the patient.

To protect the drug dosage forms from exposure to moisture either from humidity, saliva ingress, or accidental exposure to other water based liquids, the dispensing device and the container or cartridge which houses the dosage form within the device contains a desiccant. Mechanisms to prevent drug dosage forms inside a device of the inventions from exposure to moisture include but are not limited to use of desiccants, seals, absorbents, adsorbents, wipers, and sensors.

Means for trapping or otherwise isolating saliva or moisture once it has entered the device include but are not limited to a hydrophilic wicking material or component, an absorbent or adsorbent material or component, or a desiccant material or component, a separate track or channel for moisture to collect, a separate channel to communicate moisture to the absorbents or adsorbents, or any combination of these materials or components.

A desiccant is a sorbant, in the form of a solid, liquid, or gel that has an affinity for water, and absorbs or adsorbs moisture from the surrounding, thus controlling the moisture in the immediate environment. Any commercial desiccant which, typically, take the form of pellets, canisters, packets, capsules, powders, solid materials, papers, boards, tablets, adhesive patches, and films, and can be formed for specific applications, including injection moldable plastics, find application in practicing the present invention. There are many types of solid desiccants, including silica gel (sodium silicate, which is a solid, not a gel), alumino-silicate, activated alumina, zeolite, molecular sieves, montmorillonite clay, calcium oxide and calcium sulfate, or others, any of which may be used in practicing the present invention. Different desiccants have different affinities to moisture or other substances, as well as different capacities, and rates of absorption or adsorption. Also, different types of desiccants will come to equilibrium at different relative humidities in their immediate surroundings. As a means for protecting the dosage forms and the internal portions of a dispensing device of the invention from moisture, one or more desiccants may be employed at the proboscis, in or adjacent to the dosage form, delivery pathway, in or adjacent the dosage form, tablet magazine or cartridge, in or adjacent to other components of the dispensing device, formed as an injection molded component of the dispensing device, a compressed desiccant that is pressed into location, or desiccant in any other location within or without the device.

In one preferred embodiment, the desiccant snaps into a cavity in the side of the cartridge. There are holes in the desiccant cavity that connect it to the tablet stack, exposing the tablets to desiccant and keeping them dry.

A dispensing device of the invention relies on valves, pads, seals, the rest position of push rod, proboscis design and a shroud to minimize or eliminate saliva ingress or moisture into the dispensing device during administration of the dosage form.

Valves for use in a device of the invention are typically dome/trocar type valves that provide enough sealing force to keep saliva and/or moisture from entering the device and serve to minimize or eliminate saliva ingress or moisture by closing the distal orifice during dispensing and once a tablet has been dispensed.

Pads for use in a device of the invention have various geometries that aid in contacting or communicating with the pushrod in order to removed liquid from the push rod surface. Such pads typically contain hydrophilic properties and serve to minimize or eliminate saliva ingress or moisture ingress by transporting the liquid away from the track and push rod.

Seals/wipers for use in a device of the invention are designed to maintain a uniform seal around a drug dosage form and a pushrod during delivery and are characterized by flexible materials that impart a seal around the dosage form and pushrod and serves to minimize or eliminate saliva ingress or moisture by sealing and wiping the orifice and pushrod before, during, and after dispensing.

The rest position of the push rod for use in a device of the invention is characterized by positioning the pushrod in an intermediate location distal to the cartridge exit, and proximal to the distal dispensing orifice and serves to minimize or eliminate saliva ingress and moisture by allowing the pushrod to reside in a location that contains a desiccant, absorbents, or channel that dries the pushrod while at rest between dosage dispenses.

The proboscis design for use in a device of the invention is characterized by a distal device shape, typically an S-shape, that aids in use of the device and/or placement of the tip on the oral mucosa of the subject. The shape typically has curves, angles, and geometries such that it enables proper use of the device and placement of the dosage form on the oral mucosa of the subject, e.g., in the sublingual space.

The shroud of a device of the invention has a geometry that forms a barrier between the device and the oral mucosa and tongue, a relief for dosage form delivery, and an interior that is hydrophobic or hydrophilic and serves to minimize or eliminate saliva ingress or moisture ingress by creating a barrier from the oral mucosa contacting the valve area and dosage form, aiding in dosage form dispensing and discouraging dosage form adherence to the shroud. The shroud may have a rounded interior surface or other geometries to mitigate the dosage form adhering to the shroud. The shroud limits the ability of the tongue or sublingual mucosa to contact the dosage form dispensing area, thereby controlling saliva contact and ingress.

Figure 2:
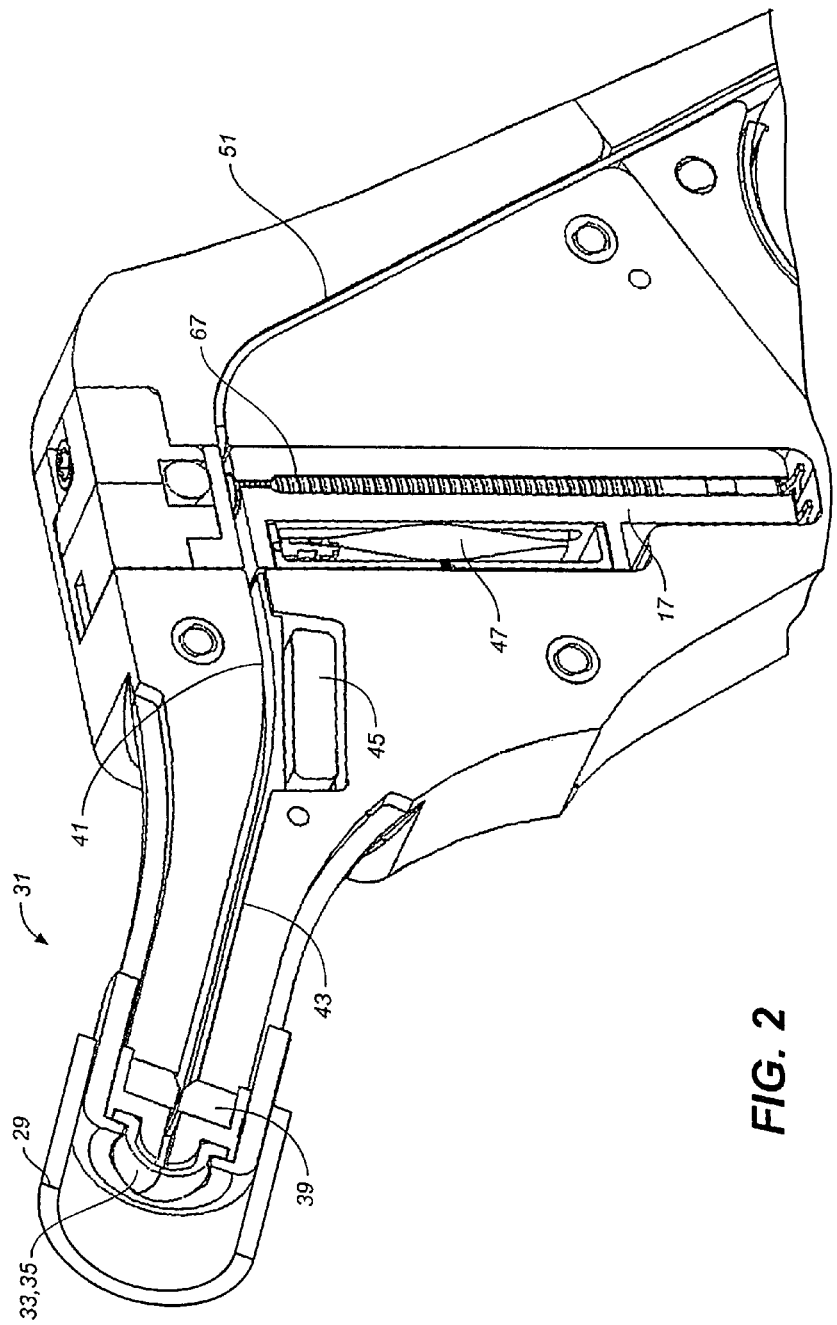
FIG. 2 is a schematic depiction of an exemplary dispensing device of the invention showing features designed to block or retard saliva and moisture ingress. The preferred embodiment includes a dispensing tip having a shroud 29, having one or more of: a wiping seal/valve 33, 35, an absorbent pad 39, a pushrod 51, a drying chamber/moisture communication channel 43, desiccant in the channel 45, a cartridge 17 containing dosage forms 67 and desiccant in the cartridge 47.

FIG. 2 is a schematic depiction of an exemplary dispensing device of the invention wherein the dispensing tip comprises a shroud 29 having a one or more of: a wiping/sealing valve 37, an absorbent pad 39, a drug drying chamber/moisture communication channel 43, desiccant in the channel 45, a cartridge 17 containing dosage forms 67 and desiccant in the cartridge 47.

Figure 3A:
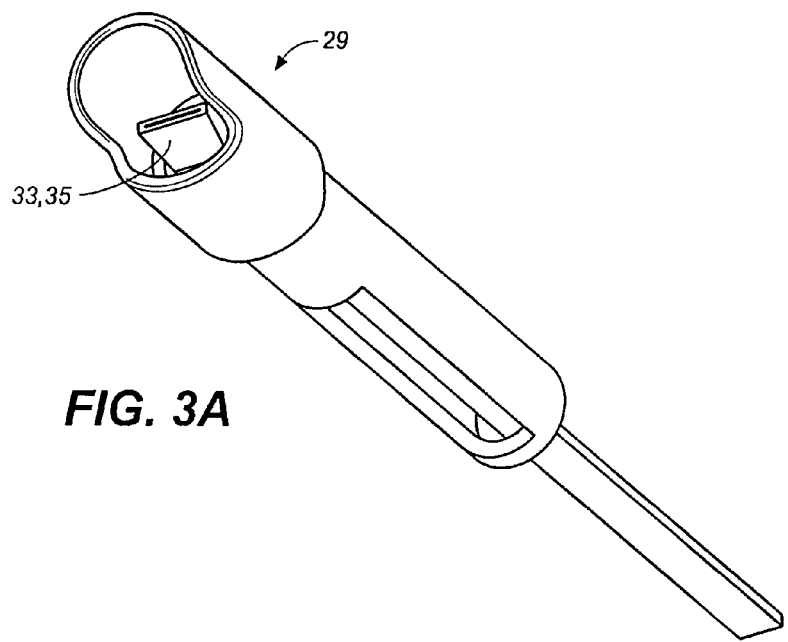
FIGS. 3A and 3B are schematic depictions of an exemplary geometry for a dispensing tip.
Figure 3B:
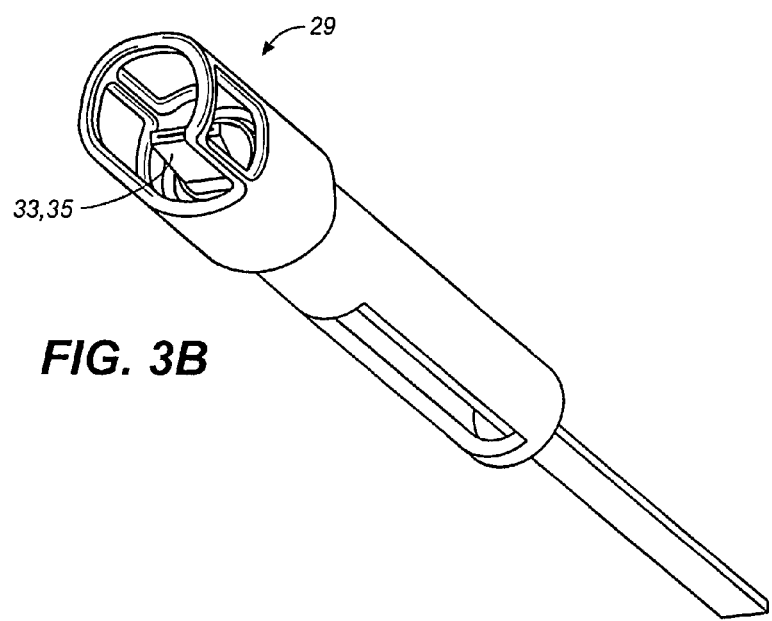
Figure 4A:
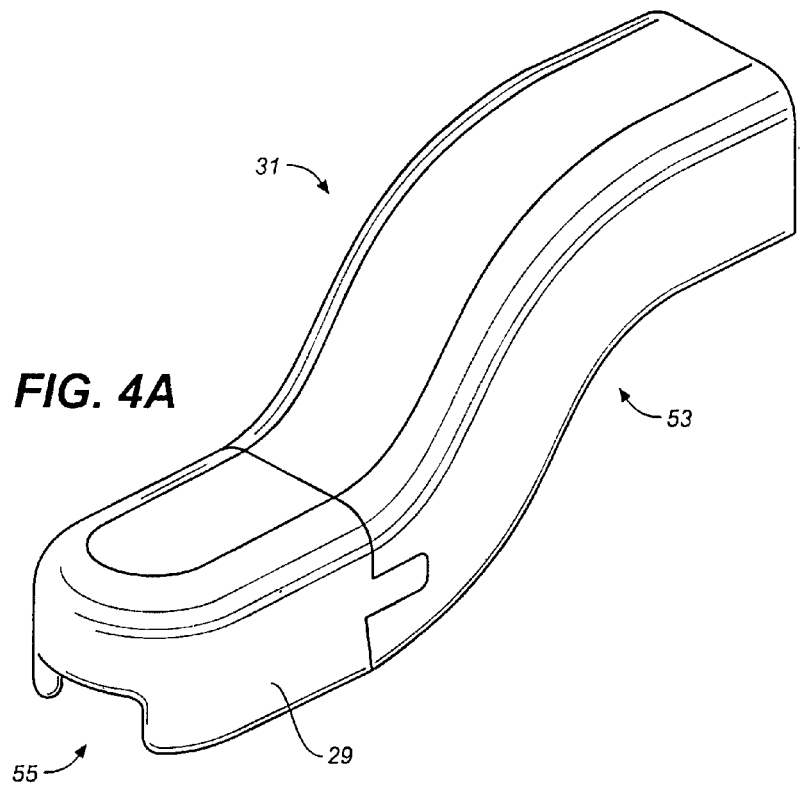
FIGS. 4A-D are a schematic depiction of an exemplary proboscis 31 of a dispensing device 11 of the invention wherein the proboscis 31 has an S-shape 53 and comprises a shroud 29 and a valve 33. The shroud shields the valve from moisture and saliva ingress from the tongue and other mucosa and provides an area for the dosage form to exit the device without "sticking" to the wetted distal valve or shroud area. The shroud also comprises a cut-out/relief 55 in order to mitigate the dragging of dosage forms when the device is removed from the oral space. The valve functions with the shroud to control saliva and moisture ingress, as well as aid in delivery of the dosage form.
Figure 4B:
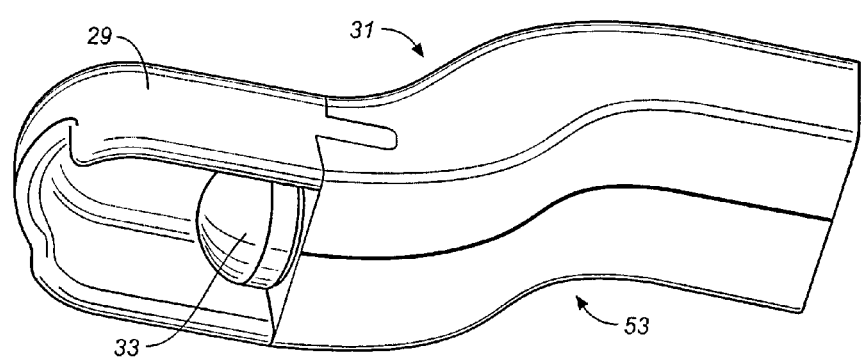
Figures 4C, 4D:
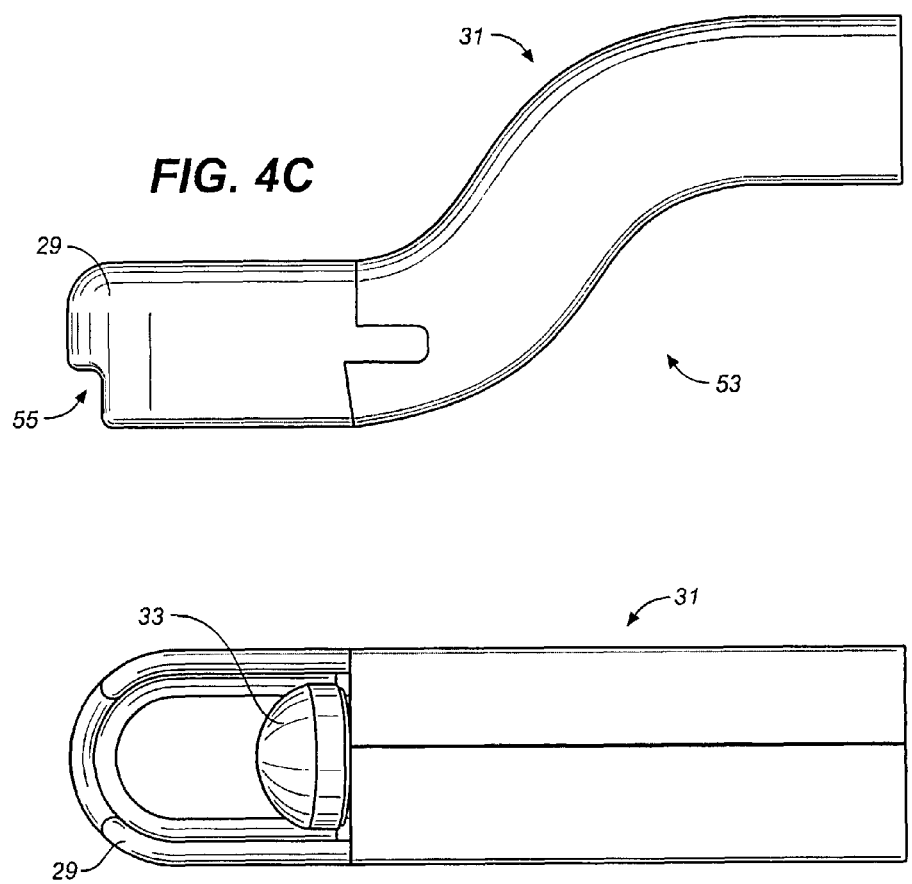

FIGS. 3A and 3B are schematic depictions of an exemplary geometry for a dispensing tip that prevents contact of one or more seals 33, 35 with the moist or wet surface of the oral mucosa via a shroud 29.

FIGS. 4A-D are a schematic depiction of an exemplary proboscis 31 of a dispensing device 11 of the invention wherein the proboscis 31 comprises a shroud 29, a valve 33 for dispensing a dosage form 67 and a cut-out/relief 55 for the dosage form 67 to be placed against the oral mucosa and not moved when the device 11 is withdrawn following dispensing.

A means for minimizing saliva ingress and moisture into a dispensing device of the invention is important for preservation of the integrity of dosage forms during storage, e.g., between oral transmucosal administrations.

A drug dosage dispensing device of the invention may be used to administer a drug dosage form that is sensitive to moisture and/or humidity. In such cases, there is a need for a drug dosage form cartridge that protects the drug dosage form from liquid and vapor phase moisture, including humidity, liquid moisture, saliva, mucus, etc. The cartridge may be cylindrical, disk-shaped, helical, rectilinear, non-ordered, or may take the form of any assemblage of drug dosage forms that allows the drug dispensing device to dispense them in a controlled manner. To prevent the unused drug dosage forms from absorbing moisture or otherwise becoming exposed to moisture prior to use, the cartridge may provide a means of sealing the drug dosage forms from exposure to moisture. This may accomplished by use of a cartridge that contains individually packaged drug dosage forms separated by a thin impermeable foil or impermeable material such that when one drug dosage form is dispensed from the cartridge, the seal protecting the remaining dosage forms remains unbroken. Alternatively, the dosage forms may be packaged in such a manner within the cartridge that two or more dosage forms are packaged together in each separate sealed compartment. In some embodiments, all of the dosage forms in a cartridge may be packaged together in a foil sealed compartment.

The drug dosage form cartridge may afford a seal against moisture by means of a septum, an elastomeric seal or valve, a sliding, translating, hinged door or valve, or by means of sealing against another component of the drug dispensing device when loaded. In this manner, a single re-sealable seal may be opened either independently or by means of the passage of a dosage out of the cartridge. Once the dosage form is delivered from the cartridge, the re-sealable seal on the cartridge may be re-sealed to prevent moisture or other contaminants from damaging the remaining drug dosage forms within the cartridge. The cartridge may further have a non-re-sealable seal that is broken when it is loaded into the drug dispensing device or upon delivery of the first dosage form from the cartridge.

In other embodiments, the cartridge contains a desiccant or other absorbent or adsorbent material to absorb or adsorb moisture that penetrates the cartridge either prior to use or during normal use. A cartridge for use in a dispensing device of the invention may contain any combination of individually sealed dosage forms, multiply sealed dosage forms, re-sealable seals, non-re-sealable seals, desiccants, absorbents, or adsorbents.

Pushrod Design

FIG. 5A shows the device LOAD logic flow. The push rod is at position A (as shown in FIG. 6), allowing the dosage forms 67 and shipping tablet 69 to be loaded into the device 11 without push rod 51 interaction. The shipping tablet 69 is at the bottom of the tablet stack 49.

Figure 7:
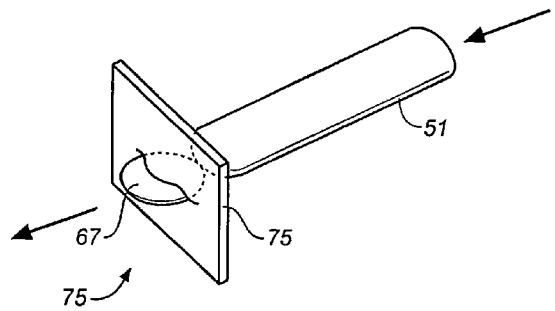
FIG. 7 is a schematic depiction of the geometry of an exemplary pushrod 51, drug dosage form 67, and septum-type seal 75.

FIG. 7 depicts an exemplary pushrod 51 designed for dispensing a drug dosage form 67. The pushrod 51 may be made from made from hydrophobic or hydrophilic materials and is generally made using flexible materials.

Figures 5C, 5D:
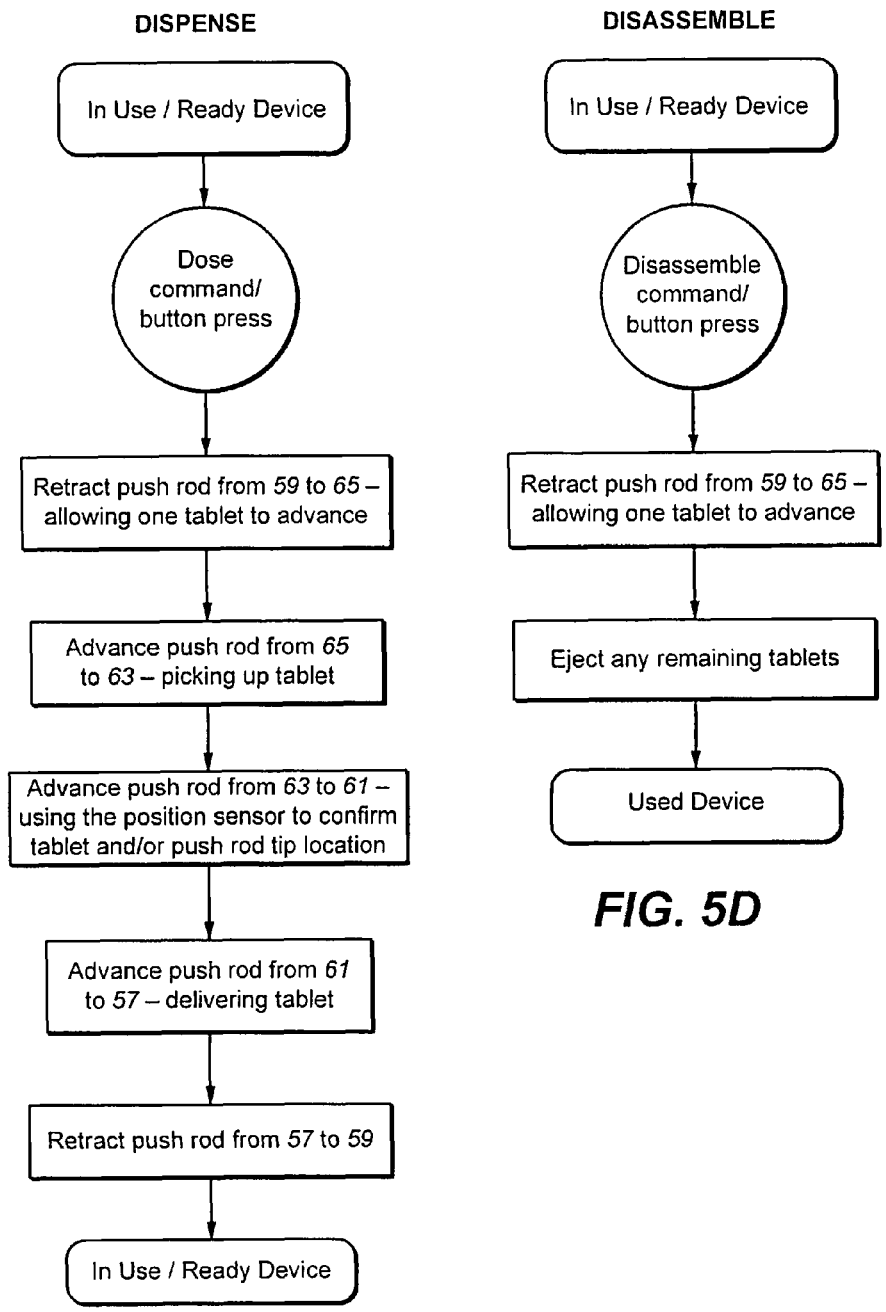
Figure 6:
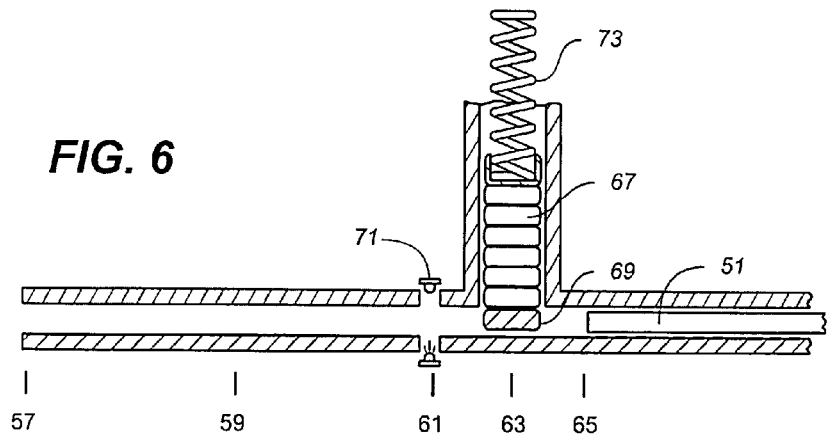
FIG. 6 is a schematic depiction of an exemplary device of the invention showing the stages of push rod/tablet interaction during device use.

FIGS. 5A-D provide a series of flow diagrams for use of an exemplary device of the invention showing pusher logic, wherein FIG. 5A shows the LOAD feature; FIG. 5B shows the device calibration logic flow. Referring to FIG. 6, the pushrod 51 is advanced from position 65, picks up the shipping tablet 69 at position 63, and is further advanced to position 61. At position 61, the device senses the presence of the shipping tablet 69 and/or push rod 51. In doing so, the device is calibrated and knows the location of the shipping tablet 69 and/or end of the push rod 51 regardless of assembly tolerances, variations in push rod length and push rod end conditions. Following this calibration, the push rod 51 advances the shipping tablet 69 from position 61 to position 57 where the shipping tablet 69 is dispensed from the device. During this operation, the device is able to distinguish between a shipping tablet 69, a push rod 51, and a drug tablet 67. This differentiation enables the device to confirm that a cartridge is unused because a shipping tablets is the first thing dispensed from a new cartridge during device setup. The feature that provides the means for differentiating between the shipping tablet, push rod, and tablet 67 may be optical, physical, RF, electronic (resistive, capacitive, or other) or magnetic. In addition, this feature may be designed to provide a means for greater device calibration precision than that attainable using a tablet or push rod. The push rod 51 advance from position 65 and position 57 described above, could be continuous or intermittent and a physical stop at position 61 is not required. The push rod 51 then retracts from position 57 to position 59, placing the device 11 in the ready position with the push rod 51 under the remaining dosage forms 67. In this position, the push rod 51 keeps dosage forms 67 from inadvertently falling out of the device 11.

FIG. 5C shows the device dispense logic flow. Referencing FIG. 6, following a dose command, the push rod 51 retracts from position 59 to position 65, allowing the tablets 67 to advance into the push rod track. The push rod 51 then advances from position 65, picks up a tablet at position 63, and then dispenses the dosage forms 67 from the device at position 57. Between positions 63 and 57, the presence of a dosage form 67 is sensed/confirmed at position 61 by the position sensor. The push rod then retracts from position 57 to position 59, placing it in the ready position with the push rod 51 is under the remaining dosage forms 67. In this position, the push rod 51 is allowed to dry before the next dosage form 67 dispense, as well as keeps dosage forms 67 from inadvertently falling out of the device 11.

FIG. 5D shows the device disassemble logic flow. Following a "disassemble" command, the push rod 51 is moved to position 65. This allows for the removal of any remaining dosage forms 67 without push rod interference.

FIG. 6 is a schematic depiction of an exemplary device of the invention showing the stages of push rod/tablet interaction during device use. In FIG. 6, the push rod 51, dosage forms 67, shipping tablet 69, spring 73 and position sensor 71 are shown. During use, the push rod 51 moves between positions 57, 59, 61, 63 and 65, also shown in FIG. 6 and further detailed in FIGS. 5A-D.

FIG. 7 depicts an exemplary pushrod designed for dispensing a drug dosage form 67 through a septum seal 75. The pushrod 51 exemplified in the figure may be made from any suitable flexible material.

Dosing History/Feedback

Further embodiments of the device include the ability to store historical use information and the ability of the device to transmit such information. The device may be capable of unidirectional (downloading) or bidirectional information transfer. For example, such an exchange of information may be accomplished by downloading stored information to a computer through a physically wired interface, such as a USB or any other communication connection. Alternatively, information may be communicated via a wireless system.

In another embodiment, the dispensing device of the invention has a dose counting feature that monitors and stores the history of drug usage. Such information may include historical use information, for example the number of dosages stored and dispensed, and the times of dispensing.

Calibration

A dispensing device of the invention may be capable of self-calibration of the dispense mechanism, or the device may be calibrated manually. This process may employ a shipping tablet with a feature or features that differentiate it from a tablet or the push rod. These features may be designed so that device calibration precision is higher that that attainable using a tablet or push rod. The differentiating feature could be physical, optical, RF, electronic or magnetic.

Patient Identification Feature

A dispensing device of the invention may comprise a detecting means for patient identification such as a fingerprint reader, an optical retinal reader, a voice recognition system, a face recognition system, a dental imprint recognition system, a visual recognition system, or a DNA reader. The dispensing device may employ one or more means to identify the user, enabling the system to determine if a dispensing request is being made in an authorized or unauthorized manner. It is important for effective delivery of many potential drugs and drug dosage forms to ensure that the dispensing device is not accidentally or intentionally used by an unauthorized individual to prevent accidental or intentional diversion of the drug. Such patient identification systems may recognize one or more users, for example, in an inpatient hospital setting the dispensing device could be programmed to recognize the patient to whom it is prescribed, as well as authorized healthcare providers such as nurses and physicians. In an outpatient home setting, for example, the dispensing device may only respond to the patient to whom it is prescribed.

The dispensing device may employ any means of user identification, including fingerprint identification, RFID detection with the use of an active or passive RFID tag on bracelet, necklace, clip, belt, strap, adhesive patch, implant, or means of locating and affixing a tag, retina identification, DNA identification, voice recognition, password or code entry, physical key, electronic or magnetic key, personal area network identification using the human body or clothing as a data or signal conduit, optical scanner or face recognition, sonic, subsonic or ultrasonic identification, or any other means of identifying an individual and verifying their identity.

One method of patient identification is the use of a short distance ("near field") passive RFID tag attached to a bracelet, necklace, adhesive patch, clothing tag, orally mounted device, like an orthodontic retainer, belt, strap, some combination of these, or another location. When an RFID tag is used in the "near field", roughly defined as about 16% of the wavelength of the received signal, the tag behaves in the inductive mode of operation, coupling between the reader and tag antenna magnetically. The near field is characterized by at least two features: first is a rapid decline in field strength with distance, and second is a strong directionality of the signal. In the near field, the signal strength falls off very rapidly, with a signal strength loss of approximately 60 dB per decade in distance. For good inductive coupling between the transmitter antenna and the RFID tag antenna, the two antennas are oriented in parallel planes with the axes through the center of each antenna in close proximity. Strong signal strength (robust patient identification) is provided when the device is very close to the RFID tag. At the same time, a very poor signal is provided when the device is further away from the tag, which helps prevent unauthorized use by someone other than the patient who attempts to use the device. It is preferable to operate in this near field region with good antenna alignment. Furthermore, it is preferable to operate with a very short distance of adequate signal strength for a positive identification, so that it is very difficult to receive a signal if the device is not in the proper orientation and proximity to the RFID tag. To attain a short distance and a proper alignment between antennas, the dispensing device may be designed so as to properly locate the RFID reader antenna, mounted in the dispensing device, adjacent to an RFID tag antenna, mounted, for example, on a wrist band or bracelet, or a clothing tag on the collar, or an adhesive patch on the hand, arm, cheek, neck, or elsewhere. Furthermore, an RFID tag antenna on a wrist band or bracelet may be held in proper alignment and location by means of a small adhesive patch that prevents the bracelet from moving or rotation on the wrist.

In another embodiment, the dispensing device employs a high frequency RFID reader for use in the inpatient (hospital, clinic, etc.) setting, operating on or near the 13.56 MHz frequency band, and the patient is be fitted with a matching RFID tag and antenna on a disposable bracelet or wrist band, designed in such a way that if the bracelet or wrist band is removed the RFID tag, the antenna, or another component of the associated circuit will be damaged or destroyed, rendering the bracelet or wrist band non-functional. In one example, the range of the RFID communication is short, between 0 inches and 10 inches preferably, more preferably between 0 and 5 inches, and most preferably between 0 and 3 inches, and may additionally be directional, allowing proper use by the intended patient to be easy and reliable, while at the same time making unauthorized use by another individual difficult, very difficult, or impossible.

In another embodiment, a dispensing device of the invention for use in the outpatient setting (e.g. home, office, etc.) includes an electronic fingerprint sensor system and would be trained to identify the patient's fingerprint at the time of prescription or first use.

Lock Out

The dispensing device may lock out at regular intervals or time periods, e.g., each day or week or two weeks, requiring the patient to communicate with the physician or other authorized care giver to unlock the device for the next fixed period. In this way the device and dock enable greater physician oversight and care management.

The dispensing device provides a means for adjusting both the initial dose and subsequent doses, as well as the lock-out time. The initial dose and lock out time may subsequently be adjusted dependent upon patient response, duration of treatment and the like.

The initial timed lock-out period for a dispensing device of the invention is typically from about 1 minute to about 60 minutes, from 3 minutes to 40 minutes or from 5 minutes to 30 minutes, and in particular cases is set at any one minute interval from 1 to 60 minutes, e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 minutes.

In some cases, a dispensing device of the invention may have a fixed lockout between doses and may exhibit a shutdown after a fixed period of time.

Additional Features

A dispensing device of the invention may provide the ability to recognize a specific cartridge by a mechanical, optical (e.g. bar code), electronic (e.g. microchip), magnetic, radio frequency, chemical, or other means of detecting and identifying the cartridge. In one exemplary embodiment of the invention, the cartridge may contain a physical keying detail on the cartridge that is physically detected by a sensor or switch or a series of sensors or switches in the dispensing device. Furthermore, the dispensing device may communicate uni-directionally or bi-directionally with the cartridge to exchange information. Such information may include drug name, dosage strength, usage information, lockout period, manufacturing lot number, indications for use, side effects, drug interactions, date of manufacture, date of expiration, serial number, number of doses in the cartridge, or any other relevant information. The dispensing device may be able to write, in addition to read, information to the cartridge, like date used, nurse or patient identification, number of doses used, etc.

A dispensing device of the invention provides mechanical protection for the dosage forms contained therein, preventing breakage, chipping, hydration etc., thereby allowing for dispensing of the undamaged dosage forms contained therein. This is of particular importance for small fragile and friable dosage forms.

A drug dispensing device may be powered by a battery, capacitor, fuel cell, or other power supply source, or may require no electrical power, but be manually activated.

In some embodiments, the dispensing device is capable of issuing alarms or other notifications when functional or safety issues arise. The alarm or other notification may trigger an alert on the dispensing device, on a dock or other peripheral device; on a computer or by means of a wired or wireless network, or may alert other remote devices. The alarm or notification may be audible, tactile, visual, or may employ other means of notifying one or more individuals.

Docking Station

In certain embodiments, the device includes a portable or fixed docking station that may query the device, reset it between dosing, lock it when not properly accessed, and control the dosing regimen. The drug dispensing device may communicate with a physician or care giver, via the dock, or by a wired or wireless communication means.

The dispensing device may employ one or more levels of interface for different types of authorized users, for example the patient, the nurse, the physician, pharmacist or other authorized medical or healthcare personnel. These different interfaces may include components such as keypads, buttons, graphical icons and instructions, lights, LED's, monochrome or color graphical or text displays, touch-screens, LCD's, sounds, tactile feedback, voice recognition interfaces, and other input and output devices and means. The activity, or mode, of the user interface may be determined by the mode of operation of the dispensing device, by a login or access activity by a user such as a password or code entry, by the connection or disconnection of the dispensing device from a dock, computer, or network, or by the detection of an authorized access key, such as a key, and/or RFID tag, or similar combination. Upon changing the interface mode, the functionality of the device may be changed, either activating, inactivating or changing the functionality of the various interface components described above. By allowing the device to have one or more interface modes, with differing functionality associated with each one, the device can be optimized for various uses.

Base Station

In some embodiments there may be a base station for recharging a drug dispensing device and the portable docking fob between uses. This base station allows for recharging the batteries or fuel cells in multiple dispensing devices and/or fobs simultaneously. In addition to recharging the drug dispensing devices and fobs, the base station may provide one or more of the following functionality: wireless or wired connectivity to a peripheral device, computer or network; feedback on the charging state for the devices being recharges; an interface for viewing, adding, deleting, or modifying the data on a drug dispensing device or fob; a means for synchronizing data between multiple drug dispensing devices and/or fobs; and a means for conducting a diagnostic test on drug dispensing devices and/or fobs.

Exemplary Dispensing devices

FIGS. 1A-E provide schematic depictions of a variety of aspects of one embodiment of a drug dispensing device of the invention. The dispensing device is constructed to hold a plurality of dosage forms for oral transmucosal drug delivery.

FIG. 1A is a schematic depiction of a fully assembled or single piece dispensing device 11 of the invention.

FIG. 1B is a schematic depiction of the dispensing device 11 for delivering drug dosage forms to a patient. In this embodiment, the dispensing device 11 includes a reusable head 13 and a disposable body 15.

FIG. 1C is a further schematic depiction of a dispensing device 11 including a reusable head 13 and a disposable body 15 and cartridge 17.

FIG. 1D is a another schematic depiction of a dispensing device 11 including a valve 33, proboscis 31, latch button 19, power train coupling 25, hub lock 21 and dispense button 23.

FIG. 1E is a schematic depiction of a reassembled and complete dispensing device 11 of the invention.

Figure 8:
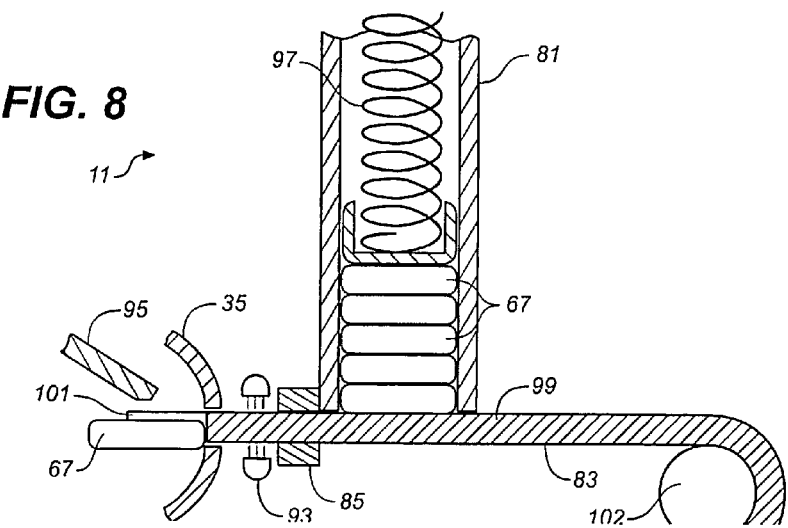
FIG. 8 provides a schematic depiction of an exemplary dispensing mechanism of a dispensing device of the invention for delivering drug dosage forms.

Fig. provides a schematic depiction of an exemplary dispensing mechanism for a dispensing device for delivering drug dosage forms. The dispensing mechanism comprises one or more of a cartridge assembly 81, a dispense button 23, a motor, a cam 83, a desiccant agent 85, seals 91, a delivery sensor 93, a spring clip 95, and a spring 97. FIGS. 8A and 8B depict the optical sensing mechanism for detecting delivery of drug dosage forms 67 of the dispensing device 11.

Figure 9A:
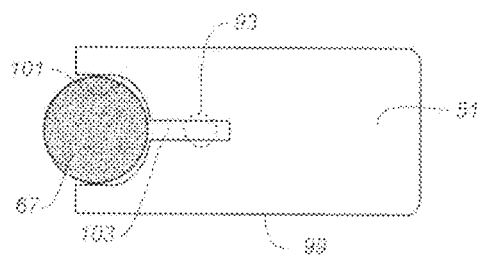
FIG. 9A is a schematic depiction of the dispensing end of a push rod 51 used to deliver a drug dosage form 67 using a dispensing device 11 of the invention.
Figure 9B:
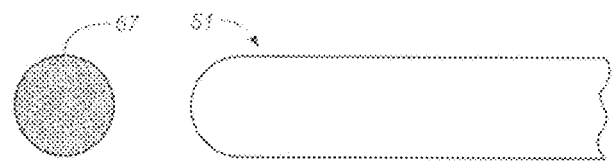
FIGS. 9B-E provide a schematic depiction of push rod embodiments for use in a dispensing device of the invention wherein the push rod may have transparent and/or reflective portions; the push rod 51 may be entirely transparent (FIG. 9B); the push rod 51 may have be opaque with or without a window 105 and with or without a reflector 106 (FIG. 9C); have a transparent tip portion 107 and an opaque push rod portion 109 (FIG. 9D); or have a transparent push rod portion 107 and an opaque tip portion 109 (FIG. 9E).
Figure 9C:
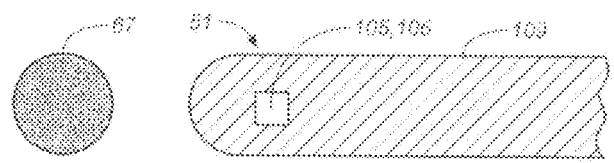
Figure 9D:
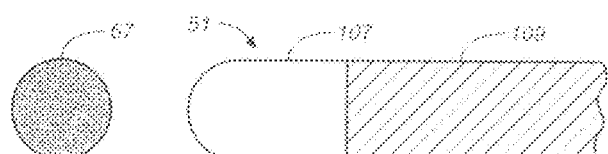
Figure 9E:
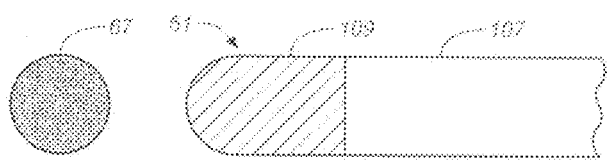

FIGS. 9B-E provide a schematic depiction of push rod embodiments for use in a dispensing device of the invention wherein the push rod 51 may be transparent 107 (FIG. 9B); the push rod may have a opaque portion 109 with or without a window 105 and with or without a reflector 106 (FIG. 9C); the push rod may have a transparent 107 tip and an opaque push rod portion 109 (FIG. 9D); or have a transparent push rod portion 107 and an opaque tip portion 109 (FIG. 9E). These approaches provide for various schemes for optical tablet and push rod position detection.

Dosage Forms

In some embodiments the present invention provides a dispensing device for repeated dispensing of a drug dosage form for oral transmucosal administration to a patient, e.g., wherein the dosage form is a Nanotab® having a size selected from the group consisting of, a volume of from about 0 to about 100 microliters, and a mass of from about 0.01 to 100 mg, a diameter of from about 1.0 to about 30.0 mm, a thickness of from about 0.25 to about 10.0 mm, and a density of from about 0.01 to 2.0 g/ml. The small-volume drug delivery dosage forms or nanotabs of the invention may have a volume of from about 0.1 to about 50, from about 0.5 to about 10.0, from 1.0 to about 25 or from about 3.0 to about 15.0 microliters, e.g., 5.0 microliters; a thickness of from about 0.25 to about 10.0 mm; from about 0.5 to about 3.0 mm, e.g., about 1.0 mm; and a diameter of from about 1.0 to about 30.0 mm, from about 1.0 to about 10.0 mm, e.g., about 2.5 mm. A typical dosage form is a substantially homogeneous composition which comprises active ingredients and one or more of bulking agents, binders, flavors, surfactants, mucoadhesins (also referred to herein as "bioadhesins"), lubricants, other excipients and factors that affect dissolution time. The present invention relates to small-volume oral transmucosal drug delivery dosage forms, dispensing devices to dispense such dosage forms and systems comprising them. The present invention provides formulations that produce a reduced saliva response when compared with other oral dosage forms, thus providing high absorption rates of the pharmaceutically active substance across the oral mucosa, and reduced delivery to the gastrointestinal tract, which is particularly useful for drugs with poor bioavailability in the GI tract.

Exemplary Nanotabs™ have a volume of from about 0 ul (microliters) to about 100 ul and a mass of from about 0 mg (milligrams) to about 100 mg. A NanoTab® of the invention is typically bioadhesive.

In one exemplary embodiment, a NanoTab™ delivered using a device of the invention has a volume of less than 30 ul, e.g., a mass of less than 5 ul, 6 ul, 7 ul, 8 ul, 9 ul, 10 ul, 11 ul, 12 ul, 13 ul, 14 ul, 15 ul, 16 ul, 17 ul, 18 ul, 19 ul, 20 ul, 21 ul, 22 ul, 23 ul, 24 ul, 25 ul, 26 ul, 27 ul, 28 ul, 29 ul or 30 ul.

In another exemplary embodiment, a NanoTab™ delivered using a device of the invention has a mass of less than 30 mg, e.g., a mass of less than 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg or 30 mg.

A NanoTab® delivered using a device of the invention finds utility in oral transmucosal administration of any drug that can be absorbed via the transmucosal route and which suffers from GI and first-pass metabolism and can therefore benefit from this dosage form and route of administration.

In one aspect, a device of the invention contains a NanoTab® comprising from about 0.25 µg to 99.9 mg, from about 1 µg to 50 mg, or from about 1 µg to 10 mg of a drug.

In another aspect, a device of the invention comprises a NanoTab® wherein the drug is an opioid selected from the group consisting of sufentanil, alfentanil, fentanyl, lofentanil, carfentanil, remifentanil, trefentanil, and mirfentanil.

A device or applicator of the invention is useful for dispensing any of a variety of drug dosage forms to the oral mucosa, including a solid tablet, a liquid capsule, a gel capsule, a liquid, a gel, a powder, a film, a strip, a ribbon, a spray, a mist, a patch, etc.

Figure 13A:
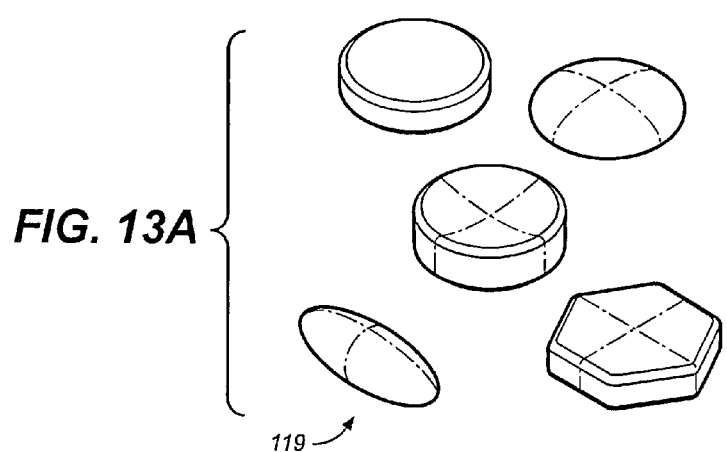
FIGS. 13A and 13B provide depictions of exemplary drug dosage form shapes.
Figure 13B:
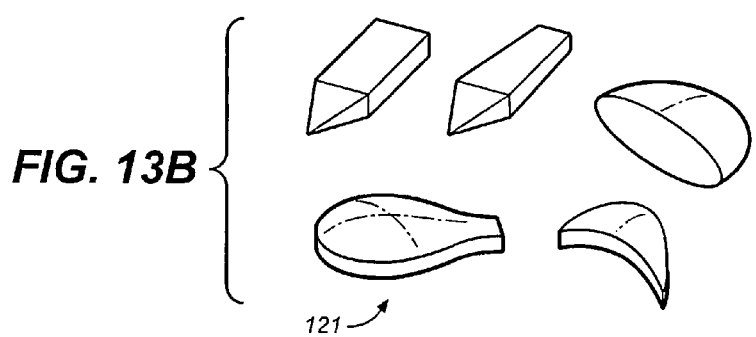

FIG. 13A is a schematic depiction of symmetric drug dosage forms 119 including round discs with flat, concave, or convex faces, ellipsoids with flat, concave, or convex faces, spherical, polygons with 3 or more edges and flat, concave, or convex faces, or any other curved solid body. FIG. 13B is a schematic depiction of asymmetric dosage forms 120.

A device of the invention can be loaded with many days worth of medication (e.g., 30 days or more) at one time, and may require no special packaging for the medication. Typically, the medication is provided in the form of a pre-filled cartridge.

Oral Transmucosal Administration

In practicing the invention, dosage forms are administered to the oral mucosa of a subject with or without a device, for example using a single or multiple dose applicator.

In one exemplary embodiment, a dispensing device of the invention is used for oral transmucosal administration of a dosage form directly to the patient in the inpatient (hospital, clinic, etc.) or outpatient setting.

In other exemplary embodiments, a dosage is administered to the patient in the inpatient (hospital, clinic, etc.) or outpatient setting using a disposable single or multiple dose applicator.

Dispensing Devices of the Invention for Oral Transmucosal Drug Delivery

Exemplary conditions treatable with a dispensing device of the invention include but are not limited to acute pain, post operative pain, cancer breakthrough pain, pre-procedural anxiety, nausea and/or vomiting.

Inpatient Setting

One use for the dispensing device of the invention arises in the inpatient setting. For example, the need for rapid treatment of acute pain occurs in many different clinical situations, including pain following an accident; post-operative pain; rheumatoid arthritis; back injury; cancer; etc. in the hospital setting. Post-operatively, for example, patients suffer from severe pain for the first few days followed by days of mild to moderate levels of pain.

Using post-operative pain as an example, a dispensing device of the invention comprises some or all of the following features: the device is a single piece that is fully disposable with an independent disposable cartridge comprising drug dosage forms; the cartridge may or may not contain one or more shipping tablets; the device is handheld and portable and has a housing with a proboscis with or without a shroud; the device has pushrod device architecture; the device has a dispensing end with a means to prevent or retard saliva ingress and to keep dosage forms stored within the device dry; the device is capable of dispensing multiple doses a single dose at a time for delivery via the oral mucosa, e.g., into sublingual space; the device may be used for self-administration or assisted administration; and the device dispensing mechanism is actuated manually.

In one embodiment of the invention, a cartridge for use in the device in the inpatient or outpatient setting may hold sufficient drug dosage forms for 1-5 days of treatment, e.g. 40 tablets useful for 48 to 72 hours of treatment.

In another embodiment the drug dispensing device is comprised of a disposable drug cartridge, a disposable dispensing end, a reusable controller end, a patient identification means like an RFID tag, a portable docking fob for controlling and accessing the drug dispensing device, and a base station for recharging the reusable dispensing end and the portable docking fob. In this embodiment the drug cartridge is loaded into the disposable dispensing end, which, in turn, is connected to the reusable controller end and affixed together. This assembly completes the drug dispensing device which is capable of dispensing dosage forms to the patient upon request, providing a lockout period between dosing, recording dosing and usage history, and allowing this history and the drug dispensing device settings to be reviewed or electronically downloaded. An RFID tag would be affixed to a patient so as to provide a wireless identification means that would enable the drug dispensing device to operate properly when in proximity to the correct RFID tag. A healthcare provider could use the portable docking fob to dock with the drug dispensing device, allowing access to settings, controls, history, and other features. When not in use, the reusable controller end and the portable docking fob could be placed in the base station to recharge the batteries or power supply.

When used in the inpatient setting, a dispensing device of the invention offers several features and advantages over the state of the art in patient drug administration. The dispensing device allows healthcare providers to provide drug dosage forms to a patient for self administration of PRN ("Pro Re Nata") medications. PRN refers to drugs that are taken as needed, such as for pain, nausea, constipation, anxiety, etc. The dispensing device of the invention may be used to dispense any PRN medication in any drug dosage form in the inpatient setting affording any combination of the features set forth above, as described in U.S. application Ser. No. 11/473, 551, which is expressly incorporated by reference herein.

Outpatient Setting

A dispensing device of the invention may also be used in the outpatient setting or in both the inpatient and outpatient setting, e.g., for treatment of post operative pain or cancer breakthrough pain. Further examples of outpatient indications where a dispensing device of the invention finds utility include chronic pain, chronic breakthrough pain, anxiety, insomnia, hypertension, coronary artery disease, depression, psychosis, addiction, ADHD, high blood pressure, diabetes and others.

In this embodiment, a dispensing device of the invention comprises some or all of the following features: the device is disposable or partially disposable with a reusable head 13, a disposable body 15 and an independent disposable cartridge 17 comprising drug dosage forms 67 (FIG. 1C); the cartridge 17 may or may not contain one or more shipping tablets 69; the device 11 is handheld and portable and has a housing with a proboscis 31 with or without a shroud 29; the device has pushrod device architecture; the device has a dispensing tip 27 with a means to prevent or retard saliva ingress and to keep dosage forms 67 stored within the device dry; the device is capable of dispensing multiple doses a single dose at a time for delivery via the oral mucosa, e.g., into sublingual space; the device may be used for self-administration or assisted administration; the device dispensing mechanism is actuated electromechanically; the device has a lock-out feature and may be child resistant; the device records dose history and is resettable by a health care provider; the device is capable of dosing feedback and dose counting; the device is capable of tablet detection/sensing, i.e. detection of when one or more shipping tablets has been dispensed; the device is capable of self-calibration of the dispense mechanism; and the device is capable of connectivity for data transfer, e.g., automatic data upload. Device calibration may or may not employ a shipping tablet with one or more features that differentiate it from a tablet or the push rod. These features may be designed such that device calibration precision is higher that that attainable using a tablet or push rod. The differentiating feature may be physical, optical, RF, electronic or magnetic.

In yet another embodiment of the invention, a dispensing device of the invention comprises some or all of the features set forth above in combination with some or all of the following features: the device has a patient identification feature, e.g., RFID; the device may monitor the temperature and shutdown if the drug dosage exceeds safe limits; the device has a display; the device has a means for connection and communication with a docking station or other docking or communication means such that the device is capable of connectivity for two-way data transfer, e.g., automatic data upload and down load via a local or remote computer system.

To effectively assist in the dispensing of drugs in the acute outpatient setting, the dispensing device may provide some or all of the following features: allow the patient to self administer the medication; record a dosing history; allow the dosing history to be read or transferred to a computer, network or other electronic device; deter tampering or diversion; deliver the drug dosage form to the appropriate location (e.g. sublingual, or buccal); record a dosing administration or a temperature or humidity event.

When used in the outpatient acute (home, office, field, etc.) setting, the dispensing device of the invention offers several features and advantages over the state of the art in outpatient drug administration. The dispensing device allows individuals to self administer drugs in accordance with physician, healthcare provider, or drug label guidelines. Some exemplary acute outpatient indications are post-operative pain, pain associated with physical trauma, anxiety, insomnia, hypertension, angina, coronary artery disease, depression, psychosis, constipation, nausea, addiction, ADHD, vertigo and others. See, e.g., U.S. application Ser. No. 11/429,904, expressly incorporated by reference herein.

The dispensing device of the invention may be used to dispense any medication in the outpatient acute setting, in any drug dosage form, affording any combination of the features set forth above. Some examples of uses for a device of the invention are in acute field care for first responders, military field medics, emergency rescue, etc.

For example, treatment of acute pain is often necessary "in the field" under highly sub-optimal conditions. First responders, such as paramedics or military field medics, often are required to treat severe acute pain in non-sterile situations, where needles used for IV or IM administration can result in unintended risk, such as infection, and so on. The dispensing devices, methods and systems of the present invention find utility in this setting.

Single and Multiple Dose Applicators

The invention provides disposable applicators for delivering dosage forms to the oral mucosa such that application to a pre-determined location for drug delivery (e.g. the mouth, sublingual space, etc.) is effected.

In one approach to the invention, a dosage form, for example, a NanoTab™ may be delivered to the oral mucosa, using a single dose applicator. The dosage form is provided in a child-resistant drug dispensing device or packaging and delivered to the oral mucosa, for example, the sublingual cavity, with supervision/assistance. Alternatively, the dosage form is administered with supervision/assistance with or without a device.

In one embodiment, a single dose applicator (SDA) is used to administer variety of drug dosage forms, including a solid tablet, a liquid capsule, a gel capsule, a liquid, a gel, a powder, a film, a strip, a ribbon, a spray, a mist, a patch, or any other suitable drug dosage form.

The single dose applicator (SDA) may contain the dosage form within, may have the drug dosage form attached or affixed to it, may have the dosage form dissolved in it, and may afford a seal against moisture, humidity, and light. The single dose applicator may be manually manipulated by a patient, healthcare provider, or other user to place the dosage form in the proper location for drug delivery.

In practicing the invention, a single- or multiple-dose applicator or drug dispensing device may be used to deliver tablets or other dosage forms into the hand, the mouth, under the tongue, or to other locations appropriate for specific drug delivery needs.

In one embodiment, a single- or multiple-dose applicator or drug dispensing device is used to deliver a dosage form to the oral mucosa, e.g., the sublingual space.

The dosage forms inside the dispensing device remain dry prior to dispensing, at which point a single dosage form is dispensed from the device into the mouth, e.g., the sublingual space, wherein a patient's saliva will wet the tablet and allow for tablet disintegration/erosion and drug dissolution.

The SDA may be provided as a pair of forceps, a syringe, a stick or rod, a straw, a pad, a dropper, a sprayer or atomizer, or any other form suitable for the application of a single drug dosage form. After use, the SDA may be disposed of, so as to eliminate the risk of contaminating the drug dispensing device with saliva, or other contaminants.

In one aspect of the invention, a small volume dosage form according to the present invention is placed in the sublingual cavity, preferably under the tongue on either side of the frenulum linguae, such that it adheres upon contact.

For sublingual administration, a small volume dosage form may be administered sublingually by placement under the tongue, adjacent to the frenulum using forceps. Alternatively, a small volume dosage form may be administered sublingually by placement under the tongue, adjacent to the frenulum using a syringe, a stick or rod, a straw, a dropper, or any other form suitable for the application of a single drug dosage form, including but not limited to a SDA, as further described herein.

The dosage forms may be provided in a package that consists of molded plastic or laminate that has indentations ("blisters") into which a dosage form, is placed, referred to herein as a "blister pack". A cover, typically a laminated material or foil, is used to seal to the molded part. A blister pack may or may not have pre-formed or molded parts.

In one embodiment, the blister pack has two flexible layers that are sealed with the dosage form in between and the primary unit dose blister pack also serves as an applicator for delivering a single dosage form to the sublingual space, once the child-resistant foil is peeled back.

In yet another embodiment of the invention, a long tape or array of dosage forms sealed between a flexible blister layer and a foil or otherwise breakable layer is provided. A push rod is positioned above a dosage form, and upon actuation pushes against the blister, forcing the dosage form through the foil or breakable layer, dispensing the dosage form.

Such blister packs may be provided in a child resistant multiple dosage drug dispensing device.

The general use of blister packs for dispensing medications is known. For example, U.S. Pat. No. 5,348,158 (Honan et al.) discloses a reusable dispensing package for the successive dispensing of tablets, pills and capsules in a predetermined sequence. A blister pack containing the medication is placed in a hinged container which rotates such that a tablet, pill or capsule contained in the blister pack is released in a predetermined sequence.

U.S. Pat. No. 5,489,025 (Romick) discloses a drug dispensing device for dispensing unit doses of medication from a blister pack. The drug dispensing device includes a top plate and a bottom plate which holds the blister pack, where the top plate has a face area and a back area with at least one aperture for receiving a blister of a blister pack and the bottom plate has at least one dispensing aperture in register with the blister of the blister pack.

Child resistant multiple dosage blister packs wherein a bottom panel has a plurality of orifices each housing individual dosages above an orifice, such that one can push individual dosages from the blister pack through an orifice have been described for example in U.S. Pat. No. 6,726,053 (Harrold).

Single patient dose medicament drug dispensing devices have been described wherein a single dose disposable drug dispensing device comprising a tray with wells containing the substance or substances to be administered are provided together with an applicator where a portion of the applicator extends beyond the open end of the applicator well. The applicator well is uncovered or squeezed to extrude the substance or substances to be administered. See, e.g., U.S. Pat. Nos. 5,660,273; 6,959,808; 6,116,414; 6,328,159.

In another approach electronic foil circuitry mounted on the lidstock of a blister package is used to detect dosing from a blister pack (U.S. Patent Publication No. 20050122219).

Although these patent publications disclose blister packs for dispensing medications, such drug dispensing devices would not be effective to deliver a dosage form to an oral mucosal membrane, e.g., to the sublingual space.

Figure 16A:
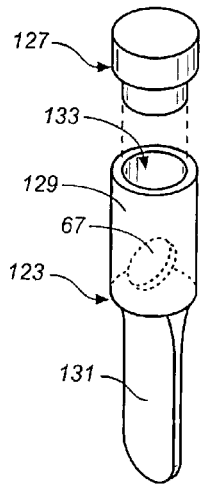
FIGS. 16A-F provide an illustration of six additional single dose applicators.
Figure 16B:
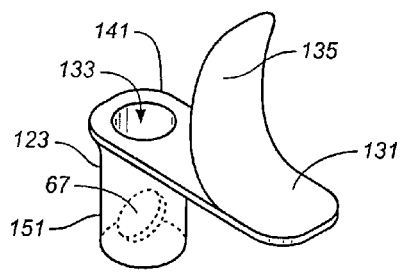
Figure 16C:
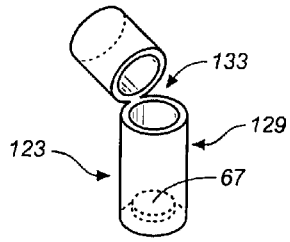
Figure 16D:
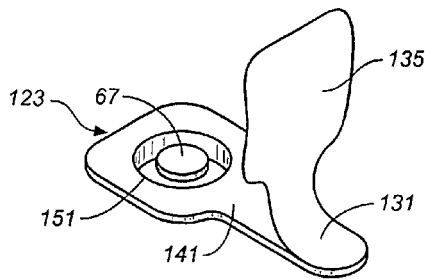

The present invention provides disposable single dose applicators comprising a blister pack 151, which contains drug dosage forms 67 inside a housing and a handle 131, wherein a backing, such as a foil seal 135 covers the dosage form 67 and the handle 131, as shown for example in FIGS. 16B and 16D.

In one embodiment, the disposable single dose applicator, the combination of housing or tube 129 and handle 131 has the shape of a spoon.

The housing or tube 129 for the dosage form 67 is a blister pack 151 that accommodates a unit dose of a dosage form 67 for administration to a subject. The dosage form 67 is sealed in the blister pack 151 by a foil or other type of seal 135 backing.

In some embodiments, the foil or other type of seal 135 is removed prior to administration of the dosage form 67 and the handle 131 is used to place the dosage form 67 in the appropriate location against the oral mucosa of the subject such that the dosage form 67 adheres to the oral mucosa. See, e.g., FIGS. 16B, 16D, 16E and 16F. In other embodiments, the foil or other type of seal 135 is perforated and removed prior to administration of the dosage form 67 by folding the applicator 123 at the perforation 149 prior to administration where the handle 131 is used to place the dosage form 67 in the appropriate location against the oral mucosa of a subject. See, e.g., FIGS. 19A and B. This permits the handling of only a single drug dosage form 67 at a time and prevents the other individually sealed drug dosage forms 67 from becoming exposed to saliva, humidity and the like.

The foil or other type of seal 135 of a disposable applicator 123 including handle 131 is typically made of a single piece of foil laminate, paper, plastic or other covering, i.e. an applicator tab 147 that spans the back of the housing or tube 129 alone or both the housing or tube 129 and the handle 131, effectively seals the dosage form 67 in a blister pack 151 or other container.

The handle 131 enables proper placement of the dosage form 67 without touching the dosage form 67.

A plurality of single dose applicators may be provided as a series of individual single dose applicators attached by the backing or housed in multiple dose dispenser 137.

In another embodiment, a dispensing device 11 comprises a package 141 that holds a single or multiple drug dosage forms, a distal orifice for delivery of the drug dosage form, and an internal mechanism that segregates and releases the dosage forms. See, e.g., FIG. 17. The dispensing device is typically handheld and may comprise some or all of the features set forth above for a device used to dispense non-packaged dosage forms.

Figures 14A, 14B:
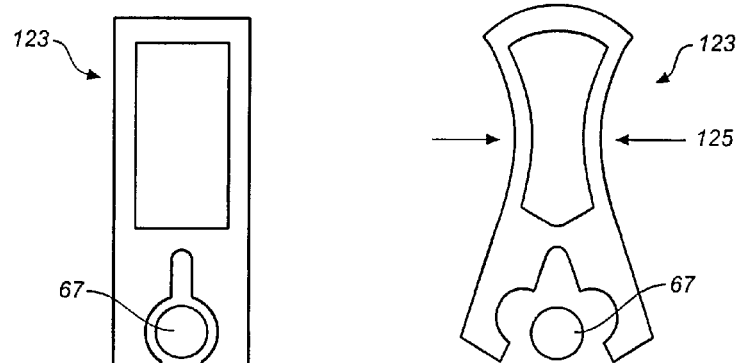
FIGS. 14A and 14B are schematic depictions of an exemplary single dose applicator.

FIGS. 14A-B are schematic depictions of exemplary single dose applicators 123 for delivering dispensing drug dosage forms 67, wherein exemplary single dose applicators are shown. When the applicator 123 is positioned for delivery and is squeezed 125, as shown in FIG. 14B, a flexible hinged section deforms, allowing the dosage from 67 to be released on an oral mucosal membrane, e.g., into the sublingual space. After applying the dosage form 67, the drug dispensing device may be disposed.

FIGS. 14A and 14B show one embodiment of a single dose applicator 123 a dispensing device for delivering drug dosage forms. The dispensing device shown in FIG. 14A depicts the single dose applicator 123 that is ready to dispense a drug dosage form 67. In one aspect of this embodiment, a user pinches the single dose applicator 125 which opens the applicator and a drug dosage form 67 is dispensed as shown in FIG. 14B.

FIGS. 15A-C, FIGS. 16A-F, FIGS. 18A-C and FIGS. 19A and B are schematic depictions of exemplary embodiments of a SDA of the invention.

Figure 15C:
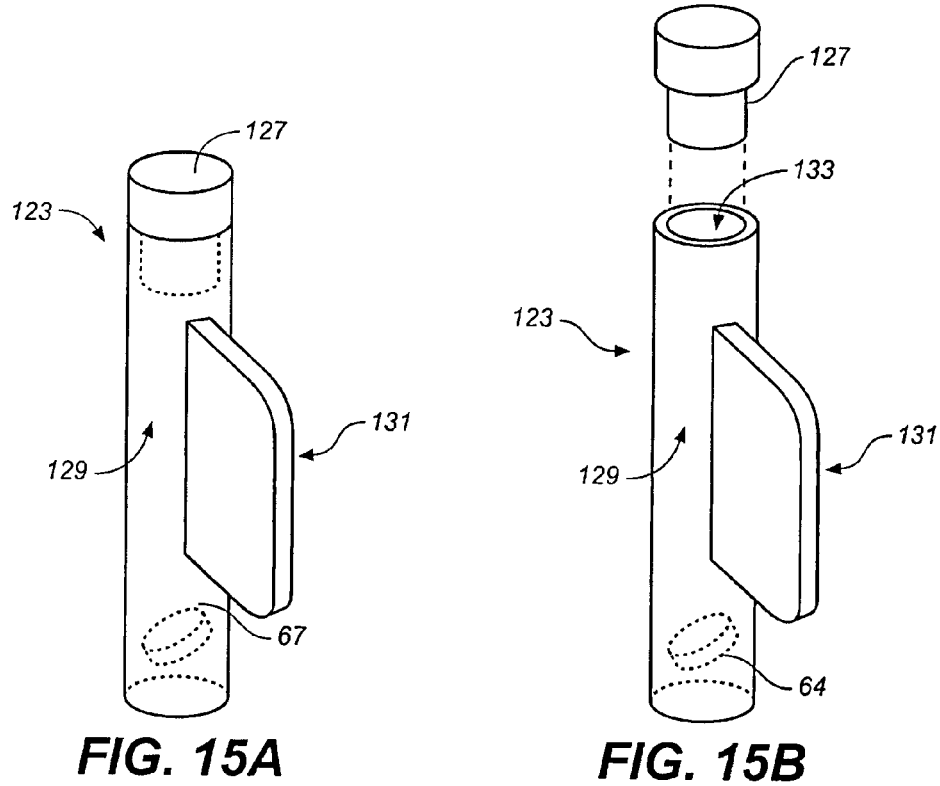
Figure 15C:
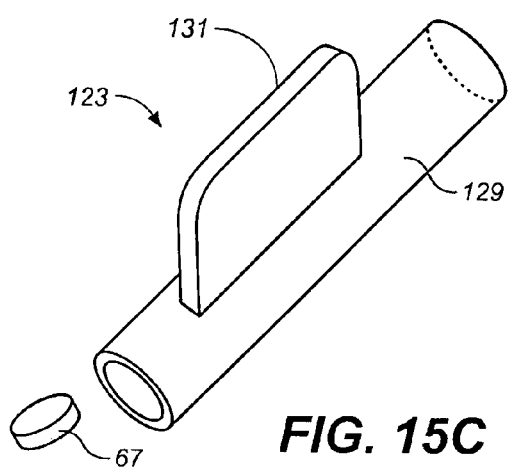

FIGS. 15A-C show an embodiment of a single dose applicator 123 that is comprised of a applicator shaped as a tube 129, a stopper seal 127, a handle 131 (e.g., an ergonomic handle), and a single dosage form 67. FIG. 15A shows the single dose applicator 123 in its sealed configuration, prior to use. FIG. 15B shows the single dose applicator 123 with its stopper seal 127 removed, forming an opening 133, and ready for use. FIG. 15C shows the single dose applicator 123 tilted so as to dispense the dosage form 67 on the oral mucosa, e.g., in the sublingual space.

Figure 16E:
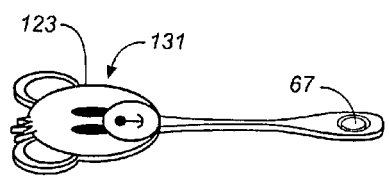
Figure 16F:
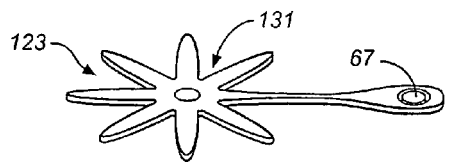

FIGS. 16A-F show several alternate embodiments of the single dose applicator 123. In all of these figures the applicator seal 127 is broken and the applicator is tilted so as to drop the drug dosage form 67 on an oral mucosal membrane in the mouth of a subject, e.g., under the tongue for sublingual dosage form placement. FIG. 16A shows a tube like applicator 129 with a handle 131 located axially under the tube 129. FIG. 16B shows an applicator formed as a thermoform or blister package 151 with a foil seal 135 that is peeled so as to open the applicator package 141 prior to placing the dosage form 67. FIG. 16C shows an applicator that is a tube 129 which is broken to break the seal prior to dosage form 67 placement. FIG. 16D shows a blister pack tube 151 type dosage form package 141 with a handle 131 such that after the seal 135 is peeled back the blister pack 151 can be held and tilted to place the drug dosage form 67, on an oral mucosal membrane. FIGS. 16E and 16F show blister pack 151 type packaging with a handle 131 shaped like a flower or an animal, respectively, to be used for single dose applicator 123 designed for pediatric use. Other single dose applicator shapes could include cartoon characters, animals, super-heroes or other appropriate shapes for pediatric applications.

FIG. 18A shows a flat rigid applicator 123 with a dosage form 67 adhered to one end, for example, by means of a rapidly dissolving ingestible adhesive material 139 such that when the applicator end with the dosage form is placed under the tongue, the adhesive dissolves, the dosage form 67 is placed on an oral mucosal membrane, such as in the sublingual space, and the applicator can be removed. FIG. 18B shows an applicator 123 made from a water permeable material, impregnated with drug, forming a material and dosage form matrix. When the impregnated end of this applicator is placed under in the mouth on the oral mucosa, the moisture in the saliva dissolves the drug and delivers it transmucosally.

FIG. 18C shows a dissolving film dosage form 145 and a dosage form package with a plurality of dissolving film dosage forms 143 within it. The dissolving film dosage form 143 is removed from the package 141 and placed on an oral mucosal membrane, e.g., in the sublingual space where it dissolves and delivers the drug transmucosally.

FIGS. 19A-B provide illustrations of two stages of use of one embodiment of a single dose applicator 123. FIG. 19A shows the applicator 123 in its configuration prior to use, with the following features: applicator tab 147, perforation 149, and blister pack 151 containing a dosage form 67. In order to administer the dosage form 67, the applicator tabs 147 are bent downward at the perforations 149, forming a handle 131, and the seal 135 is peeled back to reveal the blister pack 151 and allow the dosage form 67 to be dropped on an oral mucosal membrane, e.g., in the sublingual space.

The invention provides exemplary dispensing devices with a singulator dispensing mechanism including a reusable single dose applicator. The singulator dispensing mechanisms may include the following; a reusable single dose applicator; a foil blister; rotating stations; a disk with ejectors; a ribbon peeler; a ribbon picker; disk singulators; a flexible disk; an arc or helical type single dose applicator; a pushrod stack ejector; and a rotating stack ejector.

In another embodiment, a drug dispensing device of the invention may contain a plurality of SDA's, in a cartridge or individually packaged, and may dispense a single SDA containing a single drug dosage form for use by the patient, healthcare provider, or user. The drug dispensing device may dispense single SDA's in the same way and with the same features as would be advantageous for the dispensing of single drug dosage forms described in the invention.

In yet another embodiment the multiple dose applicator 137 comprises one or more drug dosage forms 67 or single dose applicators 123, a portable power means, like a battery, a printed circuit board, a data connectivity means, and a user interface. In this embodiment the drug dispensing device may include the ability to perform one or more of the following functions: record drug dosage dispensing history, check user identification by means of fingerprint identification, RFID, voice recognition, etc., allow the dosage history to be transferred to another device, computer or network, and/or provide a lockout period between dose dispenses.

FIG. 17 is a schematic depiction of an exemplary multiple dose applicator 137 for delivering dispensing drug dosage forms 67, each individually packaged in a single dose applicator 123.

Systems for Administration of Dosage Forms to a Patient

In one exemplary embodiment, the present invention provides a system, comprising: (1) a dispensing device for administration of a drug dosage form to the oral mucosa of a subject, for example, a small-volume dosage form or Nano-Tab®; (2) a dosage form for oral transmucosal administration, such as a small-volume dosage form or NanoTab®; and (3) a subject.

In another exemplary embodiment, the system for administration of dosage forms to a patient using a drug dispensing device of the invention includes a drug dispensing device wherein the dispensing device includes a means for reducing or eliminating moisture and saliva ingress such that the drug dosage forms remain dry inside the device prior to and during use.

Additional features which may be included in a system of the invention include a docking station or other docking means, a means of communication with a computer network such as a bidirectional communication link with a local or remote computer system (wired or wireless), a pharmaceutical network monitoring and control apparatus, a computer network that stores, records and transits information about drug delivery from the device and one or more user interfaces.

Figure 10:
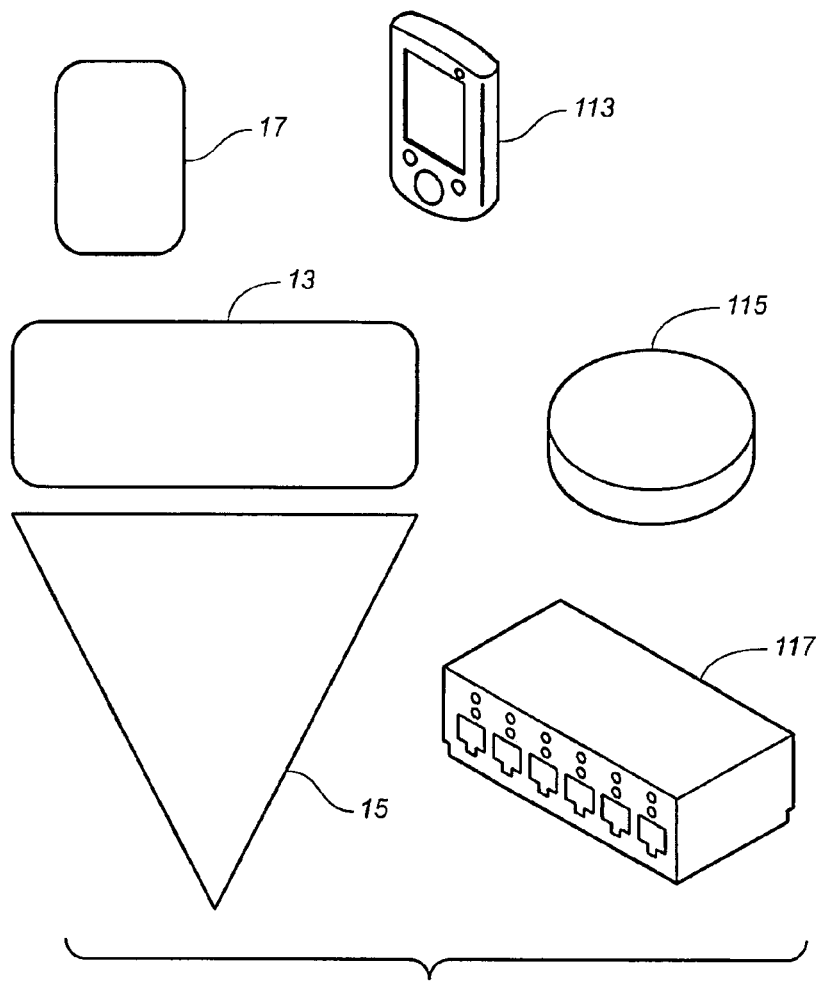
FIG. 10 is a schematic architecture connection diagram illustrating the various components that may be included in a device or system of the invention including a device with a separate drug dispensing device head 13, drug dispensing device body 15; drug cartridge 17, a portable docking FOB 113, a patient RFID tag 115, and a base station 117.

FIG. 10 is a schematic architecture connection diagram illustrating the various components that may be included in a device or system of the invention including a device with a separate head 13, body 15 and cartridge 17, a portable docking fob 113, Patient RFID 115 and a base station 117.

Figure 11:
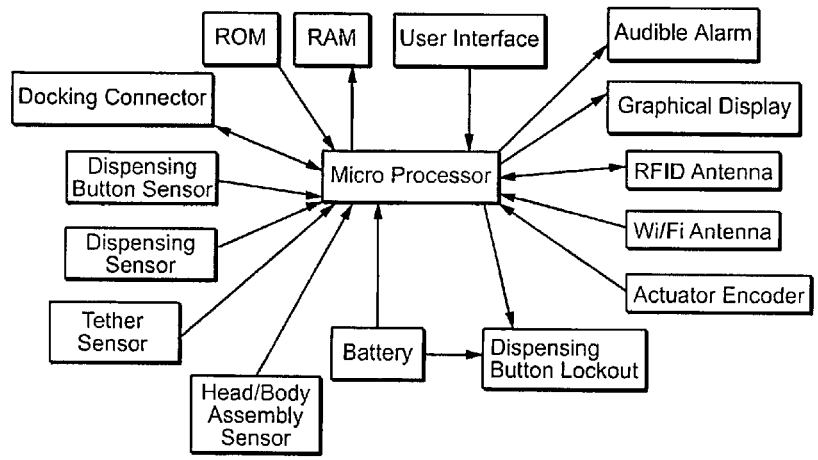
FIG. 11 is a schematic architecture connection diagram illustrating various functional elements that may be included in a drug dispensing system of the invention, including a microprocessor, which comprises RAM and ROM, a docking connector, a dispensing button sensor, a dispensing sensor, a tether sensor, a head/body assembly sensor, a battery, a dispensing button lockout, an actuator encoder, a WI/FI antenna, an RFID antenna, a graphical display, an audible alarm and a user interface.

FIG. 11 is a schematic architecture connection diagram illustrating various functional elements that may be included in a drug dispensing system of the invention, including a microprocessor, which comprises RAM and ROM, a docking connector, a dispensing button sensor, a dispensing sensor, a tether sensor, a head/body assembly sensor, a battery, a dispensing button lockout, an actuator encoder, a WI/FI antenna, an RFID antenna, a graphical display, an audible alarm and a user interface.

Figure 12A:
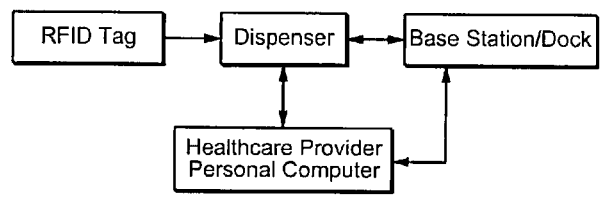
FIG. 12A is a block diagram illustrating one aspect of communication in a system of the invention, including an RFID tag, a drug dispensing device, a base station/dock and a healthcare provider personal computer.

FIG. 12A is a block diagram illustrating one aspect of communication in a system of the invention, including an RFID tag, a drug dispensing device, a base station/dock and a healthcare provider personal computer system wherein a drug dispensing device may communicate with the physician or care giver, via the dock, by means of a wired or wireless communication method.

Figure 12B:
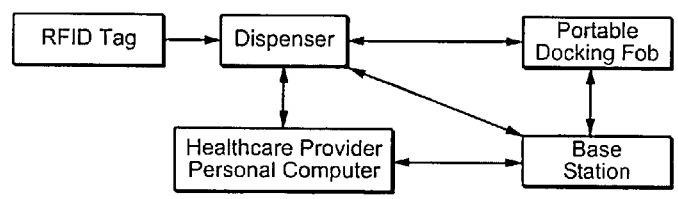
FIG. 12B is a block diagram illustrating another aspect of communication in a system of the invention, including an RFID tag, a drug dispensing device, a portable docking FOB, a base station and a healthcare provider personal computer.

FIG. 12B is a block diagram illustrating another aspect of communication in a system of the invention, including an RFID tag, a drug dispensing device, a portable docking fob, a base station and a healthcare provider personal computer. The drug dispensing device may communicate with the physician or care giver, via the fob, by means of a wired or wireless communication method to provide usage information and information regarding the respiratory status or blood pressure of the patient to the physician at regular intervals. The fob can be adapted to attach to a cord so as to allow the fob to hang from the neck of the physician or caregiver.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

EXAMPLE 1

A physician determines that a patient requires acute pain management therapy. A pharmacist loads a drug dispensing device with a drug cartridge which includes the desired strength dosage form. Each cartridge has two colored placebo dosage forms (called "shipping tablets") arranged to be the first two dosage forms dispensed. The device has a means for loading the cartridge, which is either a port, hatch, or door that is secure and inaccessible to unauthorized users. Once the pharmacist has loaded the cartridge into the device, he locks the device access port, hatch or door. The pharmacist then docks the dispensing device for the first time to a dock that is connected to a personal or other computer, using the docking connector, and then programs the device. Programming involves uploading the dosage strength of the dosage forms, the number of dosage forms loaded in the device, the prescribed frequency of dosage form usage, the number of dosage forms to be used per day, the current date and time, the preferred language, a valid thumbprint or other identification for identifying the patient, and the physician's identification information, in case the device is lost and found.

Once the dispensing device is programmed, the pharmacist demonstrates proper usage and tests the device by dispensing a single shipping tablet. The pharmacist then gives the dispensing device to the patient and observes the patient dispense a shipping tablet to ensure proper usage and functionality. Along with the dispensing device, the pharmacist provides the user with a radio frequency identification (RFID) tag that must be within approximately 5 inches of the device to allow the dispensing device to operate.

When the patient wants to administer a dose of the drug, he or she will hold the dispensing device, and push any button to wake the device up from its sleep mode. The device will query the user for either a thumbprint reading or a personal identification number (PIN). The device will then search for a validated RFID key within range. Once these conditions are met, the dispensing device will query its internal memory and clock to make sure that the dosage regimen programmed by the pharmacist is not being violated by the current usage request. At this point the device displays status information, such as the date and time, the number of doses left, the last time a dosage was used, the patient's name, etc., and the pharmacist informs the patient that the device is ready to dispense the dosage forms by a visual and/or audible signal.

The patient will hold the dispensing end of the device under his or her tongue and press the dispensing lever. When the dosage form is dispensed a tone will sound to inform the patient that the dosage form was properly delivered. At this point the device will lock down to prevent further dispensing until the preprogrammed lock-out time has passed, at which time the device will be ready to use again.

EXAMPLE 2

In a hospital environment, where a patient is under more direct supervision, a drug dispensing device wherein access and identification is limited to the detection of an RFID tag is provided. A post operative or otherwise incapacitated patient operates the device without undue physical exertion.

The dosage form dispensing device is in periodic contact with the nurse's station via wired or wireless communication (WI-FI). This allows the healthcare staff to monitor the use of the dispensing device and the number of remaining doses. The WI-FI communication allows the nurse to fully query the dispensing device at any time to see the use history and device status, including battery life, doses used, when the doses were used, doses remaining, etc.

EXAMPLE 3

A patient in a hospice takes pain medication on a regular basis. The patient's physician prescribes an oral pain medication for use with a drug dispensing device of the invention. The attending caregiver fills the prescription at an outpatient pharmacy and provides a pre-filled drug dispensing device containing sublingual analgesic tablets.

The caregiver prepares the drug dispensing device by activating the batteries, checking that the system is properly powered and confirms that the drug, dosage, and number of doses are correct by scrolling down a menu on a small display screen. The caregiver then instructs the patient on proper use and gives the drug dispensing device to the patient for patient controlled dispensing of pain medication.

When the patient requires pain medication, she takes the drug dispensing device in her hand, and places the dispensing tip in her mouth, in the buccal region, between the cheek and gum and presses the dispense button. The drug dispensing device dispenses a tablet on the patient's buccal mucosa and the patient removes the drug dispensing device from her mouth and allows the sublingual tablet to dissolve in place.

Periodically the patient or caregiver checks on the number of doses remaining in the drug dispensing device by reading the small display screen.

When the patient has dispensed all of the doses in the drug dispensing device, the counter on the display screen shows that no tablets are left and the drug dispensing device is disposed of.

EXAMPLE 4

In a post-operative recovery unit of a hospital a patient emerges from surgery requiring acute pain treatment. The surgeon prescribes an oral pain medication for use with a drug dispensing device of the invention. The attending nurse takes the prescription order to the pharmacist or automated pharmaceutical inventory management system (e.g. Pyxis) and obtains a drug cartridge containing analgesic dosage forms for oral transmucosal delivery. The cartridge is labeled and equipped with an RFID electronic tag containing drug label information.

The nurse then takes a disposable dispensing portion of the drug dispensing device from inventory, and proceeds to a base station to take a reusable controller portion of the drug dispensing device that has completed its recharge cycle is ready for use. The nurse inserts the drug cartridge into the disposable dispensing portion, and then affixes this to the reusable controller portion of the drug dispensing device and locks the disposable portion to the reusable portion of the drug dispensing device with a keyed tool. At this point the device reads the RFID tag on the drug cartridge and uploads the appropriate drug information, including the type of drug, the dosage strength, the lockout period between doses, etc. The nurse confirms the proper drug cartridge information has been read by the drug dispensing and gives the drug dispensing device to the patient for patient controlled dispensing of pain medication.

When the patient requires pain medication, she takes the drug dispensing device in her hand, and places the dispensing tip in her mouth, under her tongue and presses the dispense button. The drug dispensing device then does an internal check to ensure that the proper lockout period has elapsed since the last dosage dispense. At this point the drug dispensing device dispenses a tablet under the patient's tongue and provides a feedback that dosing was successful. The patient removes the drug dispensing device from her mouth and allows the sublingual dosage form to dissolve under her tongue. The patient may attempt to dispense as frequently as she desires, but the drug dispensing device will only allow successful dosing after the appropriate lockout period has elapsed. The drug dispensing device electronically logs the dispensing attempts and successful dispenses in its dosing history.

Periodically the nurse checks on the patient and drug dispensing device. During such a patient check in the nurse inspects the drug dispensing device to see that there are no errors and to check the number of remaining tablets in the drug dispensing device, and returns it to the patient.

When the patient is discharged, the nurse takes the drug dispensing device and unlocks the reusable portion from the disposable portion with a keyed tool, and disposes of the cartridge and disposable portion of the drug dispensing device. The nurse then connects the reusable portion to a computer and uploads the patient use information from the drug dispensing device to the computer for input into the patient's medical records. The nurse cleans the reusable controller portion and returns it to the base station for recharging.

EXAMPLE 5

In a post-operative recovery unit of a hospital a patient emerges from surgery requiring an acute pain treatment therapy. The surgeon prescribes an oral transmucosal pain medication for use with a drug dispensing device of the invention. The attending nurse takes the prescription order to the pharmacist or automated pharmaceutical inventory management system (e.g. Pyxis) and recovers a drug cartridge containing sublingual analgesic dosage forms. The cartridge is labeled and equipped with an RFID electronic tag containing drug label information. The cartridge also is loaded with a shipping tablet facsimile at the bottom, or first to be dispensed location of the tablet stack.

The nurse then takes a disposable dispensing portion of the drug dispensing device from inventory, and proceeds to a base station to take a reusable controller portion of the drug dispensing device that has completed its recharge cycle is ready for use. The nurse inserts the drug cartridge into the disposable dispensing portion, and then affixes this to the reusable controller portion of the drug dispensing device. Next, the nurse takes a portable dock (or docking fob) from the base station where it has been recharging, and docks the assembled drug dispensing device to the portable dock. The portable dock and the assembled drug dispensing device communicate electronically and a setup menu comes up on the portable dock for setting up the drug dispensing device.

At this point the device locks the reusable and disposable portions together and reads the RFID tag on the drug cartridge and uploads the appropriate drug information, including the type of drug, the dosage strength, the lockout period between doses, etc. The dispensing device writes a code to the RFID tag on the cartridge identifying it as a used cartridge. The nurse enters her fingerprint in the fingerprint reader on the portable dock to gain secured access and proceeds to set up the drug dispensing device for use. The set up procedure includes entering patient identification, the nurse's identification, confirming the proper time on the device, and confirming the proper drug cartridge information. The nurse then takes a disposable RFID bracelet and places this adjacent to the drug dispensing device at which point the drug dispensing device reads the tag and the nurse confirms that the proper bracelet tag has been read.

The nurse then confirms proper setup of the drug dispensing device by pressing the dispensing button once. The drug dispensing device actuates, dispensing the shipping tablet facsimile into the nurses hand, confirming proper operation. The drug dispensing device detects the dispensing of the shipping tablet, allowing for an internal system check of proper operation and internal calibration of the newly assembled system. If the internal dispensing check is successful, the portable dock queries the nurse to confirm that the shipping table was properly dispensed, and the nurse confirms the proper setup. The nurse then disengages the drug dispensing device from the portable dock, and proceeds to the patient's bedside for the final steps of setup.

The nurse places the RFID bracelet on the patient's preferred wrist and affixes a theft resistant tether to the patient's bed and the other end to the drug dispensing device. The nurse then instructs the patient on proper use of the sublingual PCA drug dispensing device, and gives the drug dispensing device to the patient for patient controlled dispensing of pain medication.

When the patient requires pain medication, she takes the drug dispensing device in her hand, and places the dispensing tip in her mouth, under her tongue and presses the dispensing button. The drug dispensing device then does an internal check to ensure that the proper lockout period has elapsed since the last dosage dispense, and that the patient's RFID bracelet is present and readable. At this point the drug dispensing device dispenses a tablet under the patient's tongue and provides a feedback that dosing was successful. The patient removes the drug dispensing device from her mouth and allows the sublingual dosage form to dissolve under her tongue. The patient may attempt to dispense as frequently as she desires, but the drug dispensing device will only allow successful dosing after the appropriate lockout period has elapsed. The drug dispensing device electronically logs the dispensing attempts and successful dispenses in its dosing history.

Periodically the nurse checks on the patient and device. During such a patient check in the nurse brings a portable docking fob and docks the device to the fob. The electronic connection enables the nurse to download the information from the drug dispensing device to the fob. This information includes the use history, drug information, number of remaining tablets and duration of use since initial set up. The nurse then enters her fingerprint in the finger print scanner to gain access to the information and to drug dispensing device. Because the patient is requiring an additional dose of drug prior to the lockout period expiring, the nurse overrides the lockout period and then returns the drug dispensing device to the patient at which point the patient is able to take another dose.

The nurse leaves the patient's room with the portable docking fob and returns to the nurse's station to record the dosing history in the patient's records. When finished the nurse returns the fob to the base station for recharging.

When the patient has used all of the tablets in the drug dispensing device, the nurse brings the portable docking fob into the patient's room and docks the drug dispensing device to the fob. The nurse then enters her fingerprint in the fingerprint scanner on the fob to gain secured access to the drug dispensing device. Next, the nurse unlocks the security tether and disconnects the drug dispensing device from the bed. She then unlocks the drug dispensing device and removes it from the fob for disassembly. The nurse disconnects the disposable portion from the reusable portion, and removes the cartridge from the disposable portion. The nurse disposes of the disposable portion and the cartridge, and wipes the reusable controller portion with an antiseptic wipe to clean it before returning it to the base station. The reusable controller portion requires that the nurse return it to the base station where it recharges and runs an internal diagnostic test before being ready for use again.

The nurse then proceeds to set up a new drug dispensing device as described above and provides this to the patient.

Although the foregoing invention has been described in some detail by way of illustration and example for purposes of clarity and understanding, it will be apparent to those skilled in the art that certain changes and modifications may be practiced. Various aspects of the invention have been achieved by a series of experiments, some of which are described by way of the following non-limiting examples. Therefore, the description and examples should not be construed as limiting the scope of the invention, which is delineated by the appended description of exemplary embodiments.

What is claimed is:

1. An apparatus for dispensing a drug-containing tablet to an oral mucosal membrane of a patient, comprising:
   a proboscis defining a passage through which the tablet can be passed, the passage having an exit port adjacent a distal end of the proboscis;
   a seal disposed over the exit port and configured to prevent the ingress of moisture into the exit port, the seal defining a slit configured to permit passage of the tablet therethrough; and
   a shroud disposed at the distal end of the proboscis, the shroud being extended distally past the seal, the shroud being at least partially disposed about and spaced apart from the exit port of the proboscis such that the shroud inhibits contact by a tongue and an oral mucosal membrane with the exit port.

2. The apparatus of claim 1, wherein the shroud includes a top portion disposed above the exit port and configured to be engaged with the tongue of the patient, and a side portion extending downwardly from the top portion, the side portion having a lower rim disposed below the exit port and configured to engage the oral mucosal membrane.

3. The apparatus of claim 1, wherein the shroud defines a cavity and has a lower rim disposed about a perimeter of at least a portion of the cavity and spaced from the exit port, a portion of the lower rim defining a relief sized to allow the tablet to pass therethrough to avoid engaging the tablet when the tablet is dispensed onto the oral mucosal membrane and the shroud is withdrawn from between the tongue and the oral mucosal membrane.

4. The apparatus of claim 1, wherein the shroud includes a top portion and a side portion extending downwardly from the top portion, the top portion and side portion forming a cavity being open at a bottom portion of the shroud, at least one of the exit port or the seal disposed over the exit port being extended into the cavity of the shroud such that, when the tablet is dispensed via at least one of the exit port or the seal, the tablet can fall from the at least one exit port or seal through the open bottom portion of the shroud to the oral mucosal membrane.

5. The apparatus of claim 1, wherein the shroud is configured to maintain a space between the exit port and each of the tongue and the oral mucosal membrane.

6. The apparatus of claim 1, wherein an interior surface of the shroud is hydrophilic.

7. The apparatus of claim 1, wherein an interior surface of the shroud is constructed of a hydrophilic wicking material configured to wick away moisture from within a cavity defined by the shroud.

8. The apparatus of claim 1, wherein at least a portion of an interior surface of the shroud is rounded.

9. The apparatus of claim 1, wherein the seal is at least partially disposed in a cavity defined by the shroud.

10. The apparatus of claim 1, wherein the seal is configured to maintain a uniform seal around the tablet when the tablet is passed through the seal upon exiting the exit port.

11. The apparatus of claim 1, further comprising:
    a push rod disposed in the passage for movement between a first position in which a distal end of the push rod extends from the exit port and a second position in which the distal end of the push rod is within the passage, the push rod configured to dispense a tablet from the exit port upon movement of the distal end of the push rod from the second position to the first position, and
    wherein the seal is configured to maintain a uniform seal around the push rod when the push rod is passed through the seal.

12. The apparatus of claim 1, wherein the seal is configured to wipe moisture off of a surface of a push rod as the push rod is passed through the slit of the seal.

13. The apparatus of claim 1, wherein the proboscis defines an S-shape configured to facilitate placement of the shroud beneath the tongue of the patient.

14. The apparatus of claim 1, wherein at least a portion of the passage defined by the proboscis is arcuate; the apparatus further comprising:
  a push rod, at least a portion of the push rod being sufficiently flexible to accommodate curvature of the arcuate portion of the passage when the push rod is moved within the passage.

15. A delivery tip for a device to deliver a drug-containing tablet to the oral mucosal membrane of a patient, comprising:
  a passage through which the tablet can be passed, the passage having an exit port;
  a shroud configured to be disposed within the mouth of the patient between a tongue and an oral mucosal membrane, the shroud defining a cavity about the exit port; and
  a seal disposed over the exit port and through which the tablet can be dispensed from the passage, the seal configured to prevent ingress of moisture into the exit port, the seal defining a slit configured to permit passage of the tablet therethrough during dispensation of the tablet, at least the portion of the seal defining the slit being extended into the cavity of the shroud, a portion of the shroud extending distally past the seal, the seal configured to maintain a seal about the drug-containing tablet as the tablet is passed through the slit of the seal.

16. The delivery tip of claim 15, wherein the shroud is configured to inhibit each of the tongue and the oral mucosal membrane from engaging the slit of the seal.

17. The delivery tip of claim 15, wherein the oral mucosal membrane is a sublingual membrane, the portion of the seal defining the slit is configured to be disposed in the mouth beneath the tongue and above the sublingual membrane when the shroud is disposed within the mouth beneath the tongue and above the sublingual membrane, the shroud is configured to maintain the slit of the seal spaced apart from each of the tongue and the sublingual membrane.

18. The delivery tip of claim 15, wherein at least a portion of an interior surface of the shroud is rounded.

19. The delivery tip of claim 15, wherein at least a portion of an interior surface of the shroud is hydrophilic, the hydrophilic portion configured to wick moisture away from at least the slit of the seal.

20. A delivery device for delivering a drug-containing tablet to the sublingual membrane of a patient, comprising:
  a shroud configured to facilitate sublingual dispensation of a drug-containing tablet from a delivery device, at least a portion of the shroud configured to be disposed within a mouth of a patient beneath a tongue and above a sublingual membrane, the portion of the shroud defining a cavity, at least a portion of a surface of the shroud defining the cavity being hydrophilic such that the hydrophilic surface portion is configured to wick away moisture within the cavity;
  a seal configured to seal an exit port through which the tablet can be dispensed from the delivery device to prevent the ingress of moisture into the exit port, the seal defining a slit configured to permit passage of the tablet therethrough during dispensation of the tablet, at least the portion of the seal defining the slit being extended into the cavity defined by the shroud, the shroud being extended distally past the seal, the seal configured to maintain a seal about at least one of the tablet or a push rod as the at least one tablet or push rod is passed through the slit of the seal, the seal configured to wipe moisture from a surface of the push rod as the push rod is passed through the slit of the seal;
  a delivery passage through which the tablet can be passed, at least a portion of the delivery passage having an arcuate shape, the delivery passage including the exit port; and
  a push rod at least partially disposed and movable within the delivery passage, at least a portion of the push rod being sufficiently flexible to assume the arcuate shape of the delivery passage as the push rod is moved within the delivery passage.

* * * * *